United States Patent
Jiang et al.

(10) Patent No.: US 10,618,885 B2
(45) Date of Patent: Apr. 14, 2020

(54) COMPOUNDS THAT ACTIVATE AUTOPHAGY

(71) Applicant: Macau University of Science and Technology, Macau (CN)

(72) Inventors: Zhi-Hong Jiang, Macau (CN); Li-Ping Bai, Macau (CN); Xiaobo Zhou, Macau (CN); Kam Wai Vincent Wong, Macau (CN); Zhiyuan Zheng, Macau (CN); Yuen Kwan Betty Law, Macau (CN)

(*) Notice: Subject to any disclaimer, the term of this patent is extended or adjusted under 35 U.S.C. 154(b) by 0 days.

(21) Appl. No.: 15/861,641

(22) Filed: Jan. 3, 2018

(65) Prior Publication Data

US 2019/0202802 A1  Jul. 4, 2019

(51) Int. Cl.
*C07D 401/12* (2006.01)
*A61P 35/00* (2006.01)
*C07D 413/14* (2006.01)

(52) U.S. Cl.
CPC .......... *C07D 401/12* (2013.01); *A61P 35/00* (2018.01); *C07D 413/14* (2013.01)

(58) Field of Classification Search
CPC ...... C07D 401/12; C07D 413/14; A61P 35/00
USPC ......................................................... 514/308
See application file for complete search history.

(56) References Cited

PUBLICATIONS

English Abstract Caplus DN 109:6776, Wenlong Huang. (Year: 1987).*
English Abstract DN 109:66356, Zhuoyi Hu et al (Year: 1988).*
English Abstract Caplus, Feng Meihua et al (Year: 1989).*
Wermuth et al, practice of of Medicinal Chemistry (Year: 1996).*
Tom Connors et al, Prodrugs in Cancer Chemotherapy (Year: 1995).*
Bundgaard, Prodrugs as means to improve the delivery of peptide drug. (Year: 1992).*
Huang Wenlong et al, Caplus English Abstract DN 120:68871 1993 (Year: 1993).*
Caplus English Abstract DN 111:126455 to Cai Huiming et al. 1989, 20 (1), 1-4 (Year: 1989).*
Beth Levine, et al., Autophagy in the Pathogenesis of Disease. Cell (2008), 132: 27-42.
Peidu Jiang, et al., Autophagy and human diseases. Cell Research (2014), 24: 69-79.
Zhineng J. Yang, et al., The Role of Autophagy in Cancer: Therapeutic Implications. Mol Cancer Ther (2011); 10(9); 1533-41.
N Hasima, et al., Regulation of autophagy by polyphenolic compounds as a potential therapeutic strategy for cancer. Cell Death and Disease (2014), 5: e1509.
Man Wu, et al., Guttiferone K inducesautophagy and sensitizescancercellsto nutrient stress-inducedcelldeath. Phytomedicine (2015): 902-910.

Wilfried Bursch, et al., Active cell death induced by the antiestrogens tamoxifen and ICI164 384 in human mammary carcinoma cells (MCF-7) in culture: the role of autophagy. Carcinogenesis (1996), 17(8): 1595-1607.
M. Chiara Maiuri, et al., Self-eating and self-killing: crosstalk between autophagy and apoptosis. Nature Reviews, (2007), 8: 741-752.
Qian Jia-Ding. Cardiovascular pharmacological effects of bisbenzylisoquinoline alkaloid derivatives. Acta Pharmacol Sin (2002) Dec.; 23 (12): 1086-1092.
Xiao-Yan Yang, et al., Inhibition Effect of Dauricine on Inflammatory Process Following Focal Cerebral Ischemia/Reperfusion in Rats. The American Journal of Chinese Medicine (2007), 35 (3): 477-486.
Jing Zhao, et al., Inhibitory effects of a bisbenzylisoquinline alkaloid dauricine on Herg potassium channels. Journal of Ethnopharmacology (2012), 141: 685-691.
Yan-Hong Li, et al., Neuroprotective Effects of Dauricine Against Apoptosis Induced by Transient Focal Cerebral Ischaemia in Rats Via a Mitochondrial Pathway. Clinical and Experimental Pharmacology and Physiology (2007), 34: 177-184.
Zhengfeng Yang, et al., Dauricine Induces Apoptosis, Inhibits Proliferation and Invasion Through Inhibiting NF-kB Signaling Pathway in Colon Cancer Cells. J. Cell. Physiol. (2010), 225: 266-275. Asian Pacific Journal of Tropical Medicine (2012), 973-976.
Jun Wang, et al., Dauricine can inhibit the activity of proliferation of urinary tract tumor cells.
Betty Yuen Kwan Law, et al., Natural small-molecule enhancers of autophagy induce autophagic cell death in apoptosis-defective cells. Scientific Reports (2014), 4 (5510): 1-14.
Betty Yuen Kwan Law, et al., Hernandezine, a novel AMPK activator induces autophagic cell death in drug-resistant cancers. Oncotarget (2016), 7(7): 8090-8104.
Betty Yuen Kwan Law, et al., Thalidezine, a novel AMPK activator, eliminates apoptosis-resistant cancer cells through energy-mediated autophagic cell death. Oncotarget (2017), 8(18): 30077-30091.

(Continued)

*Primary Examiner* — Rita J Desai
(74) *Attorney, Agent, or Firm* — Eagle IP Limited; Jacqueline Lui

(57) ABSTRACT

One embodiment provides a compound of Formula I that activates autophagy, a pharmaceutical composition and use thereof:

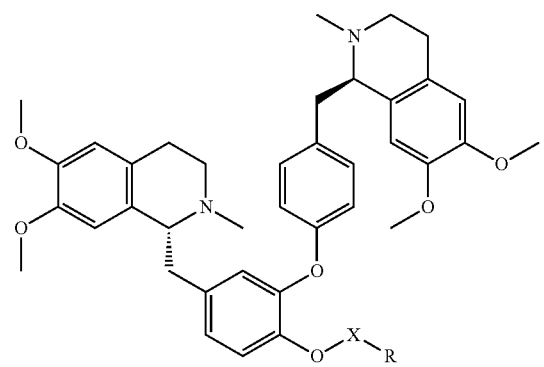

Formula I

2 Claims, 29 Drawing Sheets
(18 of 29 Drawing Sheet(s) Filed in Color)

(56) References Cited

PUBLICATIONS

Betty Y. K. Law, et al., N-Desmethyldauricine Induces Autophagic Cell Death in Apoptosis-Defective Cells via Ca2+ Mobilization. Frontiers in Pharmacology (2017), 8 Article 388.

Arun K. Ghosh, et al., Organic Carbamates in Drug Design and Medicinal Chemistry. J. Med. Chem. (2015), 58: 2895-2940.

Ker Yu, et al., Biochemical, Cellular, and In vivo Activity of Novel ATP-Competitive and Selective Inhibitors of the Mammalian Target of Rapamycin. Cancer Res (2009),69 (15): 6232-6240.

Beat Nyfeler, et al., Relieving Autophagy and 4EBP1 from Rapamycin Resistance. Molecular and Cellular Biology (2011), 31(14): 2867-2876.

Martin J. Deetz, et al., Un u su ally Low Barrie r to Carbam ate C-N Rotation. J . Org. Chem . (2002), 67: 3949-3952.

Bradley D. Smith, et al., Substituent effects on the barrier to carbamate C—N rotation. Tetrahedron Letters (2004), 45: 2747-2749.

Ming-Yue Wu, et al., Natural autophagy blockers, dauricine (DAC) and daurisoline (DAS), sensitize cancer cells to camptothecin-induced toxicity. Oncotarget (2017), 8 (44): 77673-77684.

Kevin Dalby, et al., Targeting the pro-death and pro-survival functions of autophagy as novel therapeutic strategies in cancer Autophagy (2010), 6(3): 322-329.

Sandra Turcotte, et al., Targeting cancer cells through autophagy for anticancer therapy. Curr Opin Cell Biol. (2010), 22(2): 246-251.

Akiko Kuma, et al., LC3, an Autophagosome Marker, Can be Incorporated into Protein Aggregates Independent of Autophagy: Caution in the Interpretation of LC3 Localization. Autophagy (2007), 3(4): 323-328.

Isei Tanida, et al., LC3 and Autophagy. Methods in Molecular Biology (2008), 445: 77-88.

Daniel J Klionsky, et al., Guidelines for the use and interpretation of assays for monitoring autophagy (3rd edition). Autophagy (2012), 8(4): 445-544.

VKW Wong, et al., Saikosaponin-d, a novel SERCA inhibitor, induces autophagic cell death in apoptosis-defective cells. Cell Death and Disease (2013) 4(7), e720.

John A Arnott, et al., The influence of lipophilicity in drug discovery and design. Expert Opin Drug Discov. (2012), 7(10): 863-875.

Vincent Kam Wai Wong, et al., Mechanistic Study of Saikosaponin-d (Ssd) on Suppression of Murine T Lymphocyte Activation. Journal of Cellular Biochemistry (2009), 107: 303-315.

\* cited by examiner

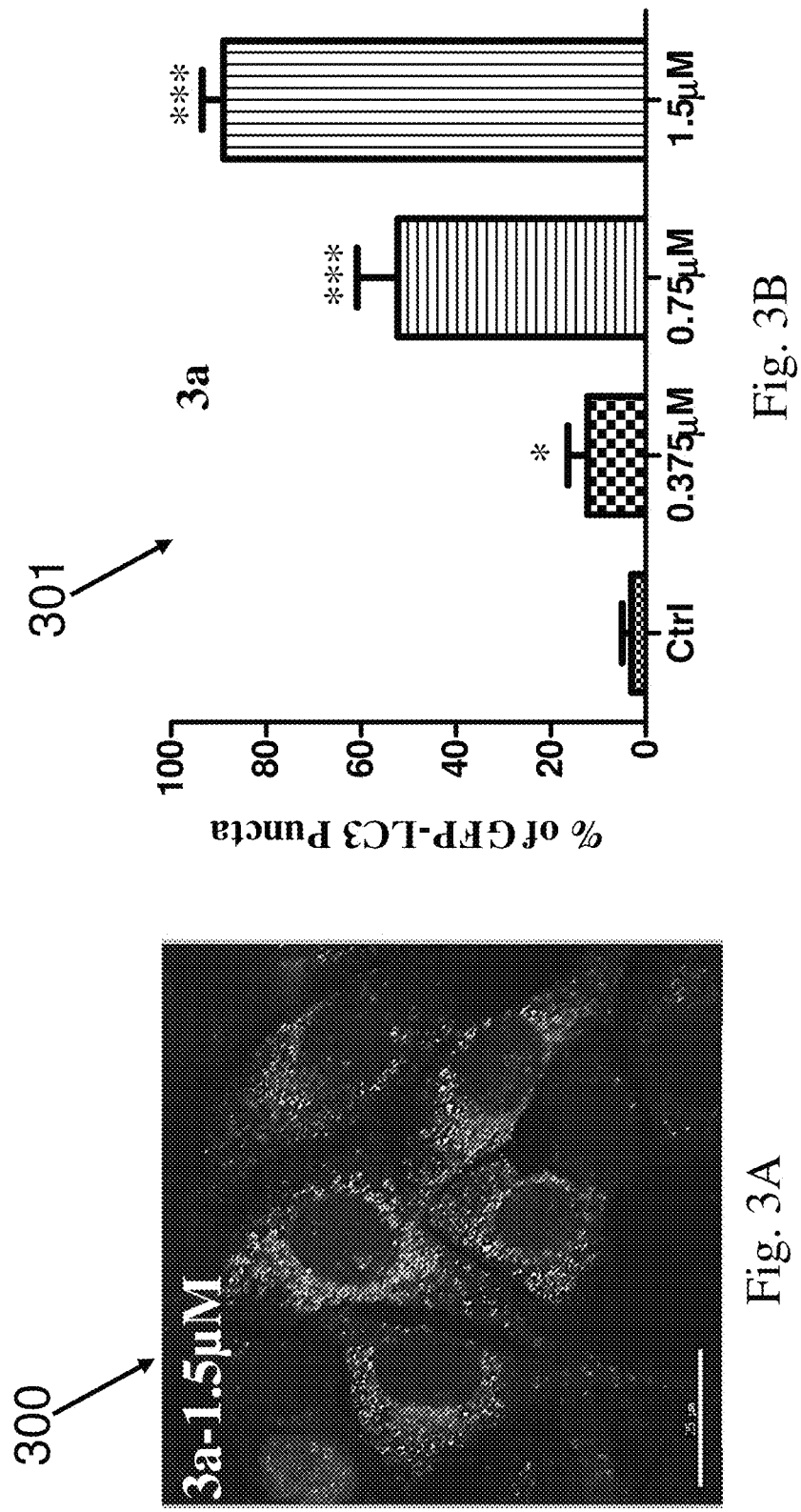

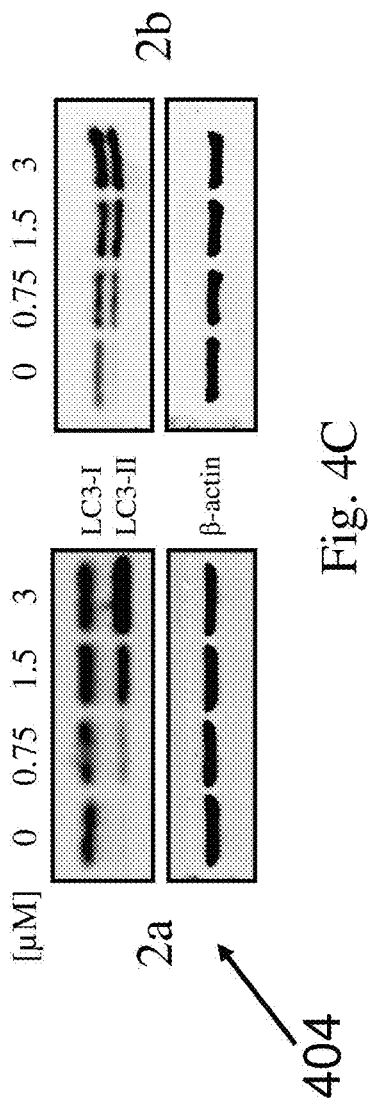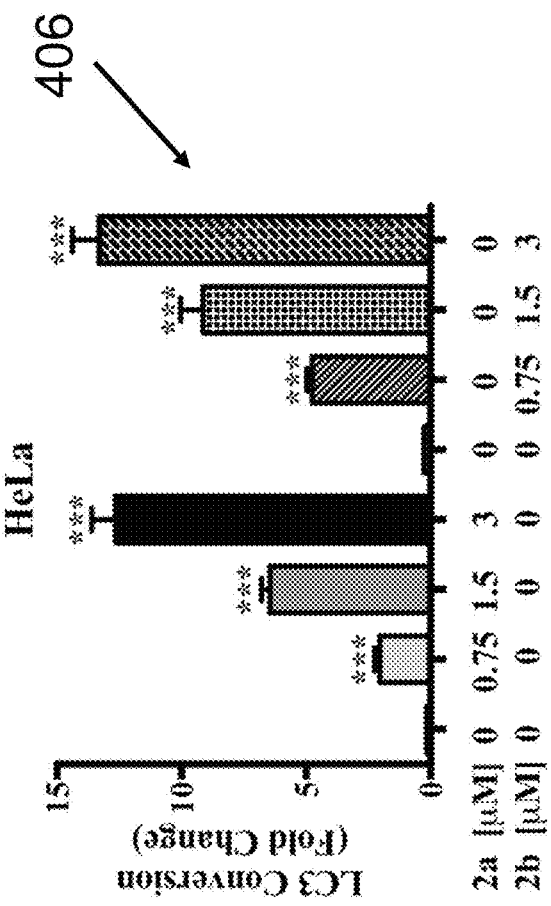
Fig. 4C
Fig. 4D

COMPOUNDS THAT ACTIVATE AUTOPHAGY

FIELD OF THE INVENTION

The present invention relates to compounds that activate autophagy. In particular, the invention relates to autophagy of cancer cells induced by the compounds.

BACKGROUND

Autophagy is a unique recycling mechanism characterized by the formation of double membrane vesicles, which engulf and degrade cytoplasmic materials or damaged organelles via lysosome degradation and thereby maintain normal homeostasis of cells. Owing to the crucial role of autophagy in cellular differentiation, development, homeostasis, starvation, and stressful conditions, defect in autophagy induction would contribute to the various diseases including neurodegenerative diseases, infectious diseases, metabolic diseases, and cancers. For cancers therapies, autophagy can act as a tumor suppressor by the removal of unfolded proteins and damaged organelles. Emerging evidence have demonstrated that polyphenolic natural compounds quercetin, genistein, rottlerin, resveratrol and guttiferone K are capable of treating cancers via the autophagic cell death mechanism.

In view of the demand for treating cancers, more compounds and compositions that can effectively treat cancers are desired.

SUMMARY

One example embodiment is to provide a compound of Formula I. The compounds are presented by the following Formula I:

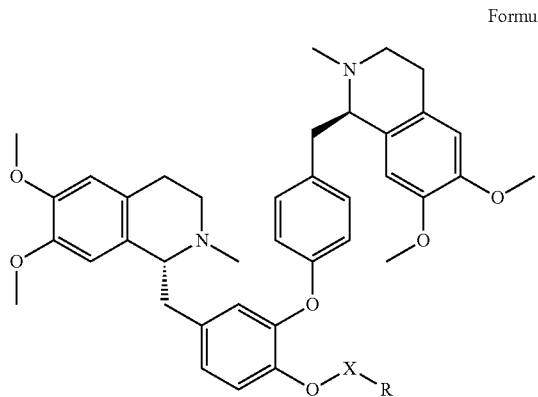

Formula I wherein:
X is —CO, or —SO$_2$;
R is hydrogen, alkyl, aryl, heteroaryl, or —NR$_1$R$_2$; and
R$_1$ and R$_2$ are independently selected from hydrogen, alkyl, aryl, alkoxy, or R$_1$ and R$_2$ together with the nitrogen atom attached thereto form a heterocyclyl, wherein the alkyl, aryl, heteroaryl, alkoxy, or heterocyclyl is optionally substituted with C$_1$-C$_6$ alkyl, C$_1$-C$_6$ alkoxy, C$_6$-C$_{14}$ aryl, or C$_2$-C$_5$ heterocyclyl, or a pharmaceutically acceptable salt thereof.

Other example embodiments are discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows autophagic activities of HeLa cells treated with compound 3a at the concentration of 1.5 µM in accordance with an example embodiment.

FIG. 3B shows a graph illustrating the percentage of GFP-LC3 puncta in HeLa cells treated with compound 3a at concentrations of 0, 0.375, 0.75, and 1.5 µM in accordance with an example embodiment.

FIG. 4C shows the western blot analysis on the autophagic marker LC3 (microtubule-associated protein 1A/1B-light chain 3) conversion in HeLa cells treated with compounds 2a and 2b at concentrations of 0, 0.75, 1.5, and 3 µM in accordance with an example embodiment.

FIG. 4D shows a quantitative graph for the western blot analysis of FIG. 4C illustrating the fold change of LC3 conversion in HeLa cells treated with compounds 2a and 2b at concentrations of 0, 0.75, 1.5, and 3 µM in accordance with an example embodiment.

DETAILED DESCRIPTION

Figure 1:
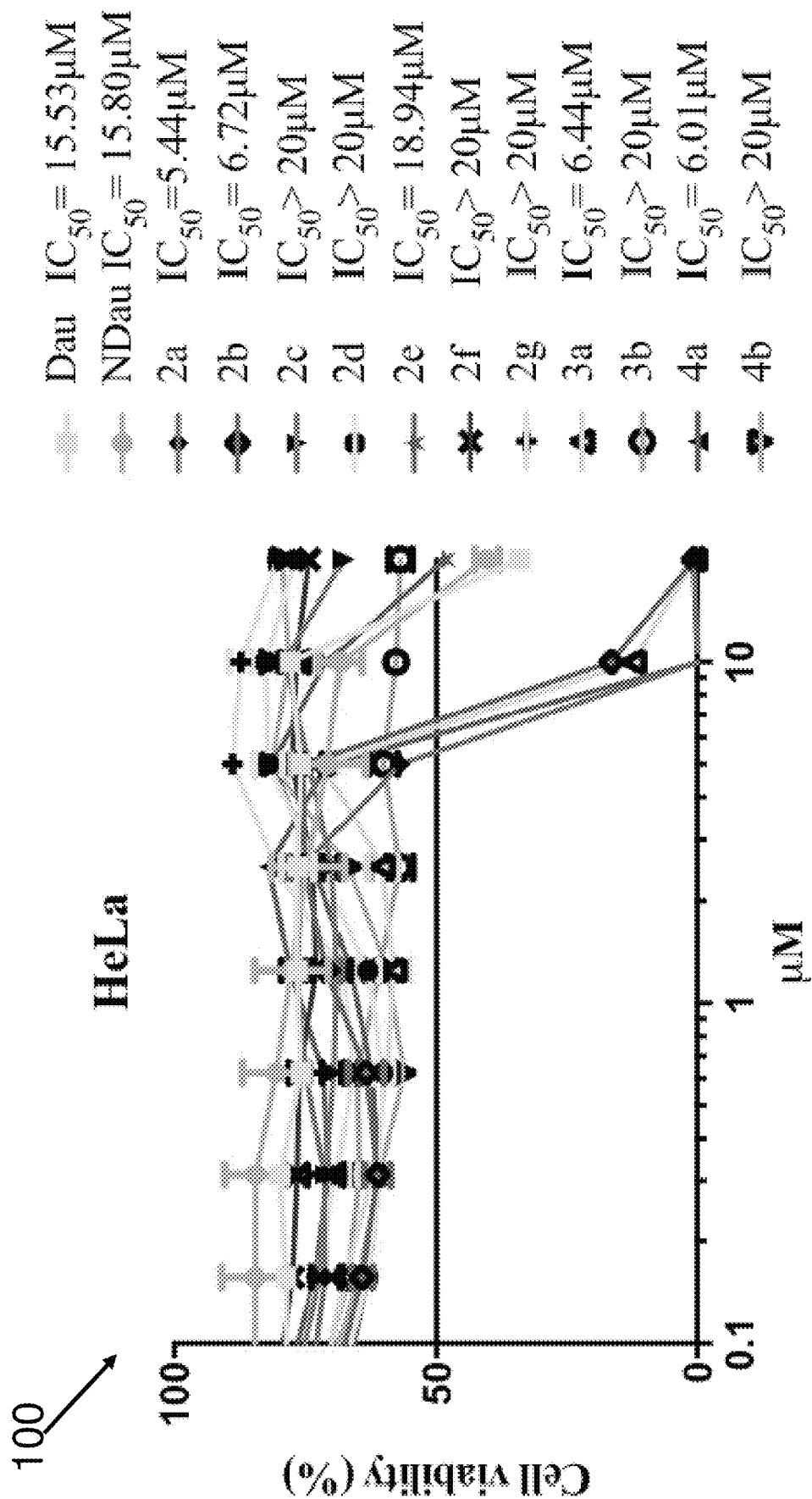
FIG. 1 shows the cytotoxicity of compounds 2a, 2b, 2c, 2d, 2e, 2f, 2g, 3a, 3b, 4a, and 4b on the HeLa cell line, compared with dauricine and N-desmethyldauricine in accordance with an example embodiment.

Example embodiments relate to a compound of Formula I, a pharmaceutical composition that includes the compound of Formula I, and a method of treating cancer by administering the compound of Formula I to a patient.

Dauricine is a bioactive bisbenzylisoquinoline alkaloid isolated from the root of *Menispermum dauricum* D.C. ("Bei-Dou-Gen" in Chinese) commonly used for the treatment of cardiac arrhythmia and inflammatory diseases in clinic. Diverse pharmacological activities of dauricine also include protection of cerebral injury, induction of cell apoptosis, suppression of cancer cell growth and angiogenesis. Previous findings have identified dauricine as an autophagy activator which stimulates autophagic cell death in a panel of apoptosis-resistant cells via AMPK (adenosine monophosphate kinase) activation. N-desmethyldauricine as a derivative of dauricine can activate autophagic cell death in Bax-Bak deficient apoptosis-defective colon cancer cells via $Ca^{2+}$ mobilization.

Conventional methods are to use dauricine and N-desmethyldauricine as autophagy activators. Example embodiments solve technical problems by providing more compounds that act as autophagy activators. Example embodiments also solve technical problems by providing compounds that are more effective than dauricine and N-desmethyldauricine in terms of activating autophagic cell death.

An example embodiment provides a compound of Formula I or a pharmaceutically acceptable salt thereof:

Formula I

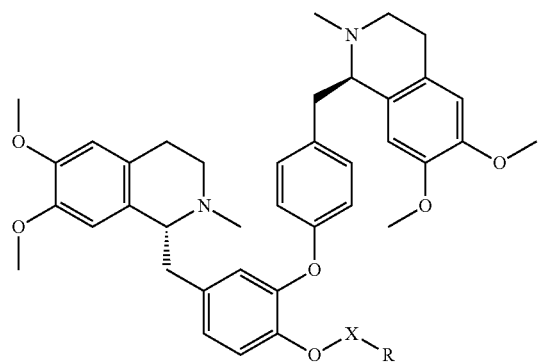

wherein:
X is —CO, or —$SO_2$;
R is hydrogen, alkyl, aryl, heteroaryl, or —$NR_1R_2$; and
$R_1$ and $R_2$ are independently selected from hydrogen, alkyl, aryl, alkoxy, or $R_1$ and $R_2$ together with the nitrogen atom attached thereto form a heterocyclyl,
wherein the alkyl, aryl, heteroaryl, alkoxy, or heterocyclyl is optionally substituted with $C_1$-$C_6$ alkyl, $C_1$-$C_6$ alkoxy, $C_6$-$C_{14}$ aryl, or $C_2$-$C_5$ heterocyclyl.

In an example embodiment, R is $C_1$-$C_6$ alkyl, $C_6$-$C_{14}$ aryl, $C_4$ heteroaryl or —$NR_1R_2$.

In an example embodiment, R is phenyl, tolyl, furyl, methyl, or —$NR_1R_2$.

In an example embodiment, R is phenyl, p-tolyl, 2-furyl, methyl, or —$NR_1R_2$.

In an example embodiment, $R_1$ and $R_2$ are independently selected from $C_1$-$C_6$ alkyl, $C_1$-$C_6$ alkoxy, $C_6$-$C_{14}$ aryl, or $R_1$ and $R_2$ together with the nitrogen atom attached thereto form $C_2$-$C_5$ heterocyclyl.

In an example embodiment, $R_1$ and $R_2$ are independently selected from phenyl, methyl, ethyl, or methoxy, or $R_1$ and $R_2$ together with the nitrogen atom attached thereto form

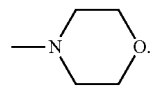

In an example embodiment, $R_1$ is phenyl; and $R_2$ is phenyl, or methyl.

In an example embodiment, the compound is selected from a group consisting of the followings: when R is —$NR_1R_2$ and X is —CO, $R_1$ and $R_2$ are both phenyl; when R is —$NR_1R_2$ and X is —CO, $R_1$ is phenyl and $R_2$ is methyl; when R is —$NR_1R_2$ and X is —CO, $R_1$ and $R_2$ are both methyl; when R is —$NR_1R_2$ and X is —CO, $R_1$ is ethyl and $R_2$ is methyl; when R is —$NR_1R_2$ and X is —CO, $R_1$ and $R_2$ are both ethyl; when R is —$NR_1R_2$ and X is —CO, $R_1$ is methoxy and $R_2$ is methyl; when R is —$NR_1R_2$ and X is —CO, $R_1$ and $R_2$ together with the nitrogen atom attached thereto form

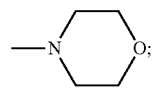

when R is phenyl, X is —CO; when R is 2-furyl, X is —CO; when R is p-tolyl, X is —$SO_2$; and when R is methyl, X is —$SO_2$.

In an example embodiment, X is —CO; R is —$NR_1R_2$; and $R_1$ and $R_2$ are phenyl. In another example embodiment, X is —CO; R is —$NR_1R_2$; $R_1$ is phenyl; and $R_2$ is methyl. In another example embodiment, X is —CO; and R is phenyl. In another example embodiment, X is —$SO_2$; and R is p-tolyl.

In an example embodiment, compounds of Formula I include compounds 2a, 2b, 2c, 2d, 2e, 2f, 2g, 3a, 3b, 4a, and 4b that are represented as the followings.

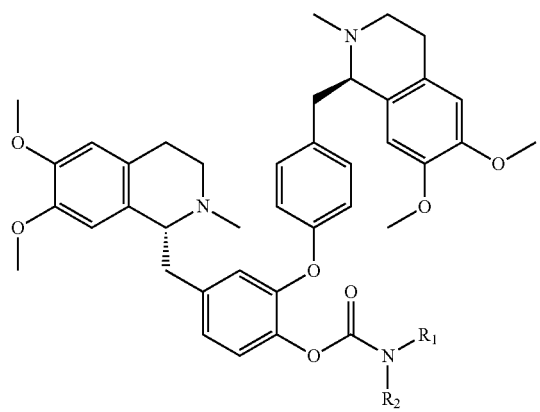

2a R1 = R2 = Ph        2d R1 = Et R2 = Me

2b R1 = Ph R2 = Me     2e R1 = R2 = Et 2 c R1 = R2 = Me       2f R1 = OMe R2 = Me 2 g R1 = R2 = 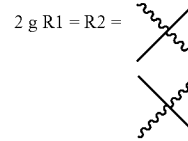

-continued

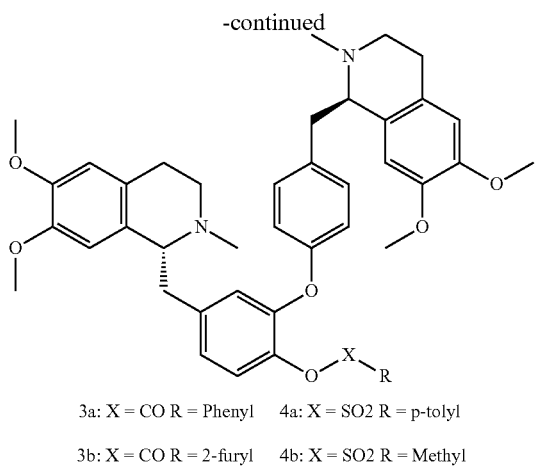

3a: X = CO R = Phenyl  4a: X = SO2 R = p-tolyl

3b: X = CO R = 2-furyl  4b: X = SO2 R = Methyl

In an example embodiment, compounds of Formula I include compounds 2a, 2b, 3a, and 4a.

An example embodiment provides a method of treating cancer, and the method includes administering the compound of Formula I to a patient.

In an example embodiment, compounds of Formula I can act as autophagy activators. Compounds of Formula I activate autophagy and induce autophagic cell death. Autophagy induction contributes to autophagic cell death in cancers including apoptosis-resistant cancers through the inhibition of anti-autophagic proteins. Compounds of Formula I induce the conversion of cytosolic LC3-I to membrane-bound LC3-II, an essential step for the induction of autophagy. Compounds of Formula I can be used to treat cancer including but not limited to liver cancer, lung cancer and cervical cancer.

In an example embodiment, compounds 2a, 2b, 3a and 4a are more effective than dauricine or N-desmethyldauricine in terms of activating autophagic cell death. Compounds 2a, 2b, 3a, and 4a can be used to treat cancer more effectively than dauricine or N-desmethyldauricine. In an example embodiment, the cancer is liver cancer, lung cancer and cervical cancer.

An example embodiment provides a pharmaceutical composition that contains the compound of Formula I.

In an example embodiment, the pharmaceutical composition includes a pharmaceutically acceptable excipient or carrier. The pharmaceutically acceptable excipient or carrier includes but not limited to fillers (diluents), binders, disintegrating agents, lubricants, and glidants.

In one example embodiment, the pharmaceutical compositions can be administered by various routes, e.g., oral, subcutaneous, transdermal, intramuscular, intravenous, or intraperitoneal. Routes of administering the pharmaceutical composition include systematic delivery or local delivery to an organ or tissue.

Example 1 Materials and Methods

Figure 7:
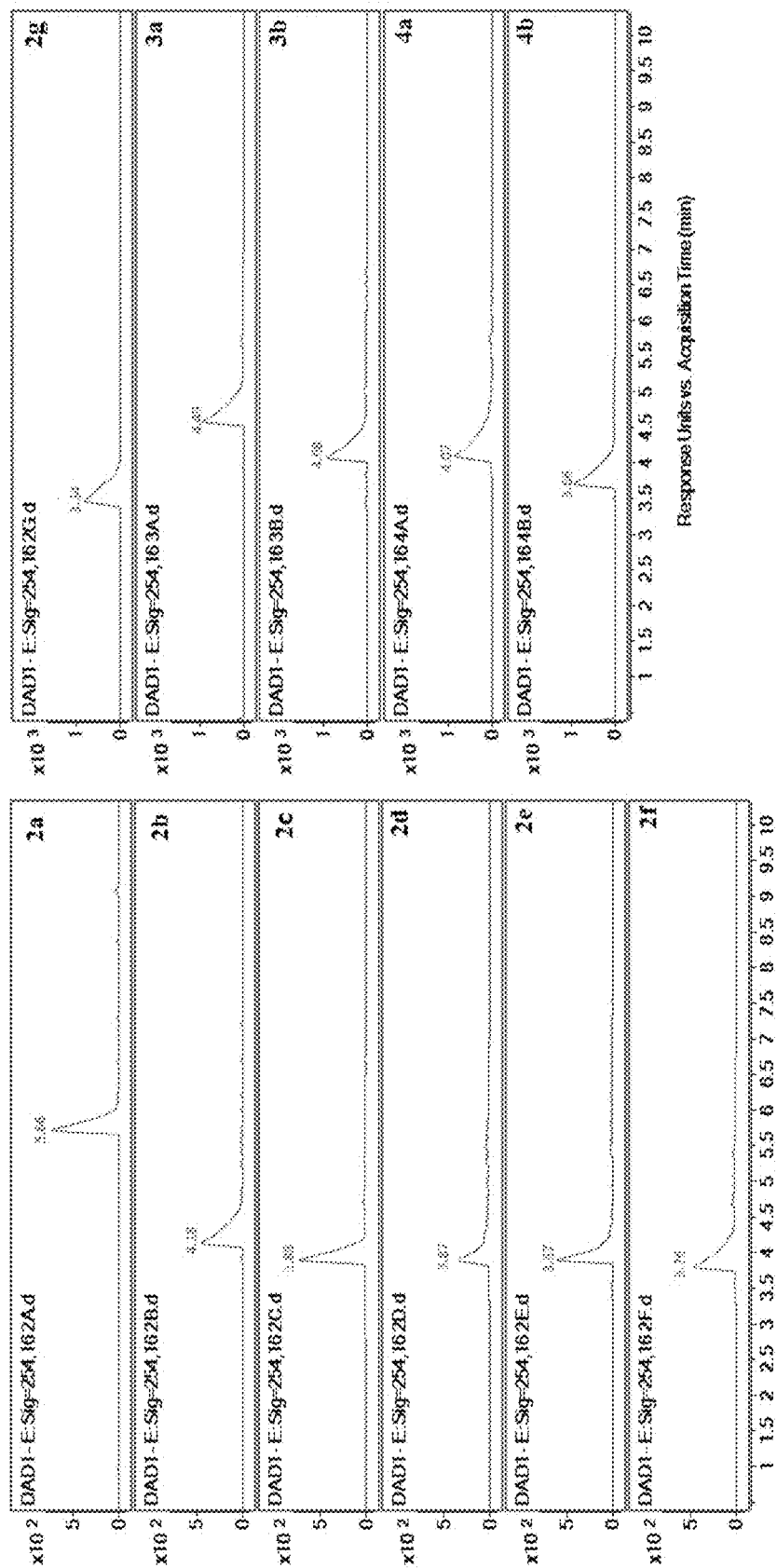
FIG. 7 shows Ultra High Performance Liquid Chromatographs (UHPLC) of compounds 2a-2g, 3a, 3b, 4a, and 4b in accordance with an example embodiment.

Synthesis of Compounds:

Eleven compounds of Formula I were synthesized. All the synthesized compounds have a purity of at least 95% determined by UHPLC-UV analysis as shown in FIG. 7. Compound 2a has a purity of 98.5%. Compound 2b has a purity of 98.2%. Compound 2c has a purity of 97.8%. Compound 2d has a purity of 96.6%. Compound 2e has a purity of 96.2%. Compound 2f has a purity of 97.7%. Compound 2g has a purity of 98.1%. Compound 3a has a purity of 98.2%. Compound 3b has a purity of 97.4%. Compound 4a has a purity of 98.1%. Compound 4b has a purity of 97.8%. The $^1$H, $^{13}$C NMR experiments were measured on a Bruker Ascend® 600 NMR spectrometer (600 MHz for $^1$H and 150 MHz for $^{13}$C) with the solvent signal as internal reference. High resolution mass spectra (HRMS) were performed on an Agilent 6230 electrospray ionization (ESI) time-of-flight (TOF) mass spectrometer. Melting points are uncorrected and were measured on a MPA100 Optimelt Point Apparatus. Column chromatography was performed with Davisil silica gel (particle size 40-63 micron). Analytical thin layer chromatography (TLC) was performed on Merck silica gel 60-F254 plates. All chemicals were purchased from 9dingchem. Unless otherwise specified, all fine chemicals were used as received. Seven newly designed carbamate compounds were synthesized following the general procedure as below (see Scheme 1).

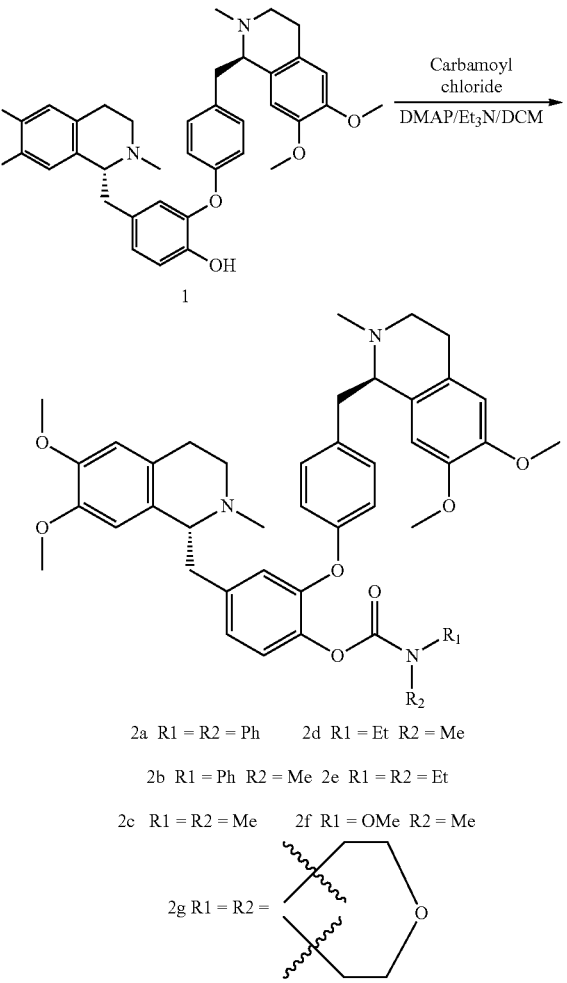

Scheme 1. Syntheses of compounds 2a-2g.

2a R1 = R2 = Ph    2d R1 = Et R2 = Me

2b R1 = Ph R2 = Me  2e R1 = R2 = Et

2c R1 = R2 = Me    2f R1 = OMe R2 = Me

2g R1 = R2 =

An equivalent of appropriate dauricine (20 mg, 0.032 mmol) was dissolved in anhydrous dichloromethane (2 mL), triethylamine (1.5 of equivalents) and appropriate carbamoyl chloride (1.2 of equivalents) were subsequently added, followed by the addition of 4-dimethylaminopyridine (DMAP; 0.1 of equivalents) as a catalyst, and then the mixture was stirred at room temperature for overnight. The reaction was monitored using TLC (Thin Layer Chromatography) detection. Finally, the reaction mixture was quenched with water and extracted with dichloromethane. Then, the dichloromethane extract was washed with brine, and further dried over $MgSO_4$. The dichloromethane solvent was evaporated and the residue was purified by chromatography on silica gel to give light yellowish solid of compounds (2a-2g).

Compound 2a: Purification by silica gel column chromatography (10:1 $CHCl_3$/MeOH) afforded 20.5 mg (78%) of 2a as light yellowish solid. TLC Rf=0.33 (10: $CHCl_3$/MeOH); Mp 105-107° C.; $[\alpha]^{24}D=-62.5°$ (c=0.2, MeOH); $^1$HNMR (600 MHz, $CDCl_3$): δ 7.28 (s, 1H), 7.25-7.27 (m, 4H), 7.21 (s, 2H), 7.20 (s, 1H), 7.17 (t, J=7.8 Hz, 2H), 7.07 (d, J=8.4 Hz, 1H), 7.04 (s, 1H), 7.04 (s, 1H), 6.85 (s, 1H), 6.84 (dd, J=8.4 Hz, 2.4 Hz, 1H), 6.84 (s, 1H), 6.68 (d, J=1.8 Hz, 1H), 6.56 (s, 1H), 6.50 (s, 1H), 6.11 (s, 1H), 6.07 (s, 1H), 3.82 (s, 3H), 3.80 (s, 3H), 3.70 (t, J=6.0 Hz, 1H), 3.63 (t, J=6.0 Hz, 1H), 3.61 (s, 3H), 3.54 (s, 3H), 3.15-3.23 (m, 2H), 3.04-3.11 (m, 2H), 2.73-2.84 (m, 5H), 2.56-2.61 (m, 2H), 2.50-2.55 (m, 1H), 2.52 (s, 3H), 2.46 (s, 3H). $^{13}$CNMR (150 MHz, $CDCl_3$): δ 155.5, 152.6, 147.8, 147.3, 147.2, 146.4, 146.4, 142.3, 140.6, 138.7, 134.7, 130.8, 128.8, 128.7, 126.2, 126.0, 125.8, 125.1, 123.2, 121.6, 117.7, 111.2, 111.1, 110.9, 110.7, 64.8, 64.5, 55.7, 55.6, 55.5, 46.9, 46.7, 42.6, 42.6, 40.7, 40.5, 25.5, 25.1. HRMS (ESI): m/z for $C_{51}H_{53}N_3O_7$ calcd 819.3884, found 820.3981[M+H]$^+$, found 410.7049 [M+2H]$^{2+}$.

Compound 2b: Purification by silica gel column chromatography (10:1 $CHCl_3$/MeOH) afforded 21.3 mg (88%) of 2b as light yellowish solid. TLC Rf=0.33 (10:1 $CHCl_3$/MeOH); Mp 93-95° C.; $[\alpha]^{24}D=-90.0°$ (c=0.2, MeOH); $^1$HNMR (600 MHz, $CDCl_3$): δ 7.25-7.28 (m, 2H), 7.15-7.20 (m, 3H), 7.05 (s, 1H), 7.04 (d, J=8.4 Hz, 1H), 7.04 (s, 1H), 6.85 (br, 1H), 6.84 (s, 1H), 6.82 (s, 1H), 6.72 (br, 1H), 6.56 (s, 1H), 6.51 (s, 1H), 6.13 (s, 1H), 6.08 (s, 1H), 3.82 (s, 3H), 3.80 (s, 3H), 3.69 (t, J=6.0 Hz, 1H), 3.64 (t, J=6.0 Hz, 1H), 3.63 (s, 3H), 3.58 (s, 3H), 3.18-3.22 (m, 1H), 3.12-3.16 (m, 1H), 3.05-3.11 (m, 2H), 2.81-2.85 (m, 2H), 2.74-2.79 (m, 3H), 2.68-2.72 (m, 1H), 2.54-2.60 (m, 2H), 2.51 (s, 3H), 2.47 (s, 3H). $^{13}$CNMR (150 MHz, $CDCl_3$): δ 155.6, 153.3, 147.8, 147.2, 147.2, 146.4, 146.4, 142.9, 140.8, 138.6, 134.5, 130.7, 129.2, 128.8, 128.8, 126.3, 126.0, 125.2, 123.3, 121.8, 111.2, 111.1, 110.9, 110.7, 64.8, 64.5, 55.7, 55.6, 55.5, 46.9, 46.7, 42.6, 42.6, 40.6, 40.5, 38.1, 25.4, 25.2. HRMS (ESI): m/z for $C_{46}H_{51}N_3O_7$ calcd 757.3727, found 758.3826 [M+H]$^+$, 379.6795 [M+2H]$^{2+}$.

Compound 2c: Purification by silica gel column chromatography (10:1 $CHCl_3$/MeOH) afforded 20.0 mg (90%) of 2c as light yellowish solid. TLC Rf=0.34 (10:1 $CHCl_3$/MeOH); Mp 110-112° C.; $[\alpha]^{24}D=-85.7°$ (c=0.2, MeOH); $^1$HNMR (600 MHz, $CDCl_3$): δ 7.07 (d, J=8.4 Hz, 1H), 7.05 (s, 1H), 7.04 (s, 1H), 6.88 (dd, J=8.4 Hz, 2.4 Hz, 1H), 6.84 (s, 1H), 6.83 (s, 1H), 6.77 (d, J=1.8 Hz, 1H), 6.58 (s, 1H), 6.55 (s, 1H), 6.14 (s, 1H), 6.12 (s, 1H), 3.86 (s, 3H), 3.84 (s, 3H), 3.69-3.73 (m, 2H), 3.68 (s, 3H), 3.63 (s, 3H), 3.20-3.25 (m, 1H), 3.14-3.18 (m, 3H), 2.93 (s, 3H), 2.86 (s, 3H), 2.83-2.87 (m, 1H), 2.75-2.82 (m, 5H), 2.56-2.63 (m, 2H), 2.53 (s, 3H), 2.51 (s, 3H). $^{13}$CNMR (150 MHz, $CDCl_3$): δ 155.9, 154.3, 147.9, 147.4, 147.3, 146.5, 146.5, 141.1, 138.4, 134.3, 130.7, 129.1, 128.8, 125.9, 125.4, 123.6, 122.1, 117.4, 111.2, 111.0, 110.8, 64.8, 64.6, 55.7, 55.6, 46.9, 46.8, 42.6, 42.6, 40.7, 40.6, 36.8, 36.3, 25.4, 25.2. HRMS (ESI): m/z for $C_{41}H_{49}N_3O_7$ calcd 695.3571, found 696.3602 [M+H]$^+$, 348.6742 [M+2H]$^{2+}$.

Compound 2d: Purification by silica gel column chromatography (10:1 $CHCl_3$/MeOH) afforded 20.9 mg (92%) of 2d as light yellowish solid. TLC Rf=0.34 (10:1 $CHCl_3$/MeOH); Mp 85-87° C.; $[\alpha]^{24}D=-108.0°$ (c=0.2, MeOH). The syn and anti rotamers' doubling signals were observed in $^{13}$C NMR due to the barrier of N—CO rotation in carbamate moiety. $^1$HNMR (600 MHz, $CDCl_3$): δ 7.10 (d, J=8.4 Hz, 1H), 7.05 (s, 1H), 7.03 (s, 1H), 6.88 (dd, J=8.4 Hz, 2.4 Hz, 1H), 6.84 (s, 1H), 6.83 (s, 1H), 6.77 (d, J=1.8 Hz, 1H), 6.57 (s, 1H), 6.54 (s, 1H), 6.15 (s, 1H), 6.15 (s, 1H), 3.86 (s, 3H), 3.84 (s, 3H), 3.69-3.73 (m, 2H), 3.67 (s, 3H), 3.63 (s, 3H), 3.28-3.32 (m, 2H), 3.17-3.23 (m, 1H), 3.10-3.15 (m, 3H), 2.81-2.85 (m, 2H), 2.80 (s, 3H), 2.72-2.76 (m, 2H), 2.56-2.62 (m, 2H), 2.53 (s, 3H), 2.50 (s, 3H), 1.08 (t, J=7.2 Hz, 3H). $^{13}$CNMR (150 MHz, $CDCl_3$): δ 156.0 (155.8), 154.1 (153.8), 147.9, 147.8, 147.3, 146.5, 146.5, 141.2 (141.1), 138.4, 134.5 (134.3), 130.7, 129.3 (129.0), 126.0, 125.5 (125.3), 123.6 (123.6), 122.3 (121.9), 117.5 (117.2), 111.2, 111.2, 111.0, 110.8, 64.8, 64.6, 55.8, 55.7, 55.6, 46.9, 46.9 (46.8), 44.1, 44.0, 42.7, 42.7, 40.7, 34.3, 33.6, 25.5, 25.3, 12.9 (12.4). HRMS (ESI): m/z for $C_{42}H_{51}N_3O_7$ calcd 709.3727, found 710.3706 [M+H]$^+$, 355.6884 [M+2H]$^{2+}$.

Compound 2e: Purification by silica gel column chromatography (10:1 $CHCl_3$/MeOH) afforded 20.4 mg (88%) of 2e as light yellowish solid. TLC Rf=0.34 (10:1 $CHCl_3$/MeOH); Mp 103-105° C.; $[\alpha]^{24}D=-81.8°$ (c=0.2, MeOH); $^1$HNMR (600 MHz, $CDCl_3$): δ 7.11 (d, J=8.4 Hz, 1H), 7.04 (s, 1H), 7.03 (s, 1H), 6.88 (dd, J=8.4 Hz, 2.4 Hz, 1H), 6.84 (s, 1H), 6.83 (s, 1H), 6.74 (d, J=1.8 Hz, 1H), 6.58 (s, 1H), 6.54 (s, 1H), 6.10 (s, 1H), 6.12 (s, 1H), 3.86 (s, 3H), 3.83 (s, 3H), 3.69-3.72 (m, 2H), 3.67 (s, 6H), 3.61 (s, 3H), 3.30-3.31 (m, 2H), 3.20-3.25 (m, 3H), 3.11-3.18 (m, 3H), 2.83-2.87 (m, 1H), 2.75-2.82 (m, 5H), 2.55-2.62 (m, 2H), 2.54 (s, 3H), 2.51 (s, 3H), 1.09 (t, J=12.6 Hz, 6H). 13CNMR (150 MHz, $CDCl_3$): δ 155.8, 153.7, 147.9, 147.4, 147.3, 146.5, 146.5, 141.2, 138.1, 134.2, 130.7, 129.0, 128.8, 125.8, 125.8, 125.3, 123.6, 121.9, 117.4, 111.2, 111.0, 110.9, 64.8, 64.6, 55.8, 55.7, 55.6, 46.8, 46.7, 42.6, 42.5, 42.2, 41.9, 40.7, 40.6, 25.4, 25.2, 13.9, 13.3. HRMS (ESI): m/z for $C_{43}H_{53}N_3O_7$ calcd 723.3884, found 724.4013 [M+H]$^+$, 362.7045 [M+2H]$^{2+}$.

Compound 2f: Purification by silica gel column chromatography (10:1 $CHCl_3$/MeOH) afforded 21.2 mg (93%) of 2f as light yellowish solid. TLC Rf=0.32 (10:1 $CHCl_3$/MeOH); Mp 84-86° C.; $[\alpha]^{24}D=-81.3°$ (c=0.2, MeOH); $^1$HNMR (600 MHz, $CDCl_3$): δ 7.12 (d, J=8.4 Hz, 1H), 7.06 (s, 1H), 7.04 (s, 1H), 6.89 (dd, J=8.4 Hz, 2.4 Hz, 1H), 6.86 (s, 1H), 6.84 (s, 1H), 6.73 (d, J=1.8 Hz, 1H), 6.58 (s, 1H), 6.54 (s, 1H), 6.14 (s, 1H), 6.09 (s, 1H), 3.86 (s, 3H), 3.83 (s, 3H), 3.68-3.73 (m, 2H), 3.66 (s, 6H), 3.63 (s, 3H), 3.19-3.22 (m, 1H), 3.18 (s, 3H), 3.10-3.17 (m, 3H), 2.83-2.87 (m, 1H), 2.75-2.82 (m, 5H), 2.55-2.62 (m, 2H), 2.53 (s, 3H), 2.51 (s, 3H). $^{13}$CNMR (150 MHz, $CDCl_3$): δ 155.5, 154.5, 148.0, 147.3, 146.5, 146.5, 140.4, 138.9, 134.7, 130.9, 130.9, 130.8, 129.1, 128.7, 125.9, 125.3, 123.3, 121.8, 117.8, 117.8, 117.7, 111.2, 111.2, 111.0, 110.8, 64.8, 64.6, 61.5, 55.8, 55.7, 55.6, 46.9, 46.7, 42.6, 42.6, 40.7, 40.6, 35.6, 25.4, 25.2. HRMS (ESI): m/z for $C_{41}H_{49}N_3O_8$ calcd 711.3520, found 712.3595 [M+H]$^+$, 356.6852 [M+2H]$^{2+}$.

Compound 2g: Purification by silica gel column chromatography (10:1 $CHCl_3$/MeOH) afforded 22.0 mg (93%) of 2g as light yellowish solid. TLC Rf=0.32 (10:1 $CHCl_3$/MeOH); Mp 104-106° C.; $[\alpha]^{24}D=-76.8°$ (c=0.2, MeOH); $^1$HNMR (600 MHz, $CDCl_3$): δ 7.10 (d, J=8.4 Hz, 1H), 7.06 (s, 1H), 7.04 (s, 1H), 6.90 (dd, J=8.4 Hz, 2.4 Hz, 1H), 6.83 (s, 1H), 6.81 (s, 1H), 6.80 (d, J=1.8 Hz, 1H), 6.58 (s, 1H), 6.55 (s, 1H), 6.18 (s, 1H), 6.14 (s, 1H), 3.86 (s, 3H), 3.84 (s, 3H), 3.69-3.72 (m, 2H), 3.67 (s, 6H), 3.66 (s, 3H), 3.52 (m, 2H), 3.48 (m, 2H), 3.40 (m, 2H), 3.18-3.21 (m, 1H), 3.10-3.18 (m, 3H), 2.78-2.85 (m, 5H), 2.73-2.78 (m, 1H), 2.57-2.62 (m, 2H), 2.52 (s, 3H), 2.51 (s, 3H), 1.96 (m, 2H). $^{13}$CNMR (150 MHz, CDCl$_3$): δ 155.8, 153.1, 147.5, 147.3, 147.3, 146.5, 140.9, 138.7, 134.5, 130.7, 129.2, 128.9, 126.1, 126.0, 125.6, 123.5, 122.3, 117.0, 111.2, 111.2, 111.0, 110.8, 66.6, 66.4, 64.8, 64.6, 55.9, 55.7, 55.7, 46.9, 46.8, 44.9, 44.2, 42.7, 42.6, 40.7, 40.7, 25.5, 25.2. HRMS (ESI): m/z for C$_{43}$H$_{51}$N$_3$O$_8$ calcd 737.3676, found 738.3748 [M+H]$^+$, 369.6919 [M+2H]$^{2+}$.

Compounds 3a, 3b, 4a, and 4b were synthesized by scheme 2.

Scheme 2. Syntheses of compounds 3a and 3b and compounds 4a and 4b.

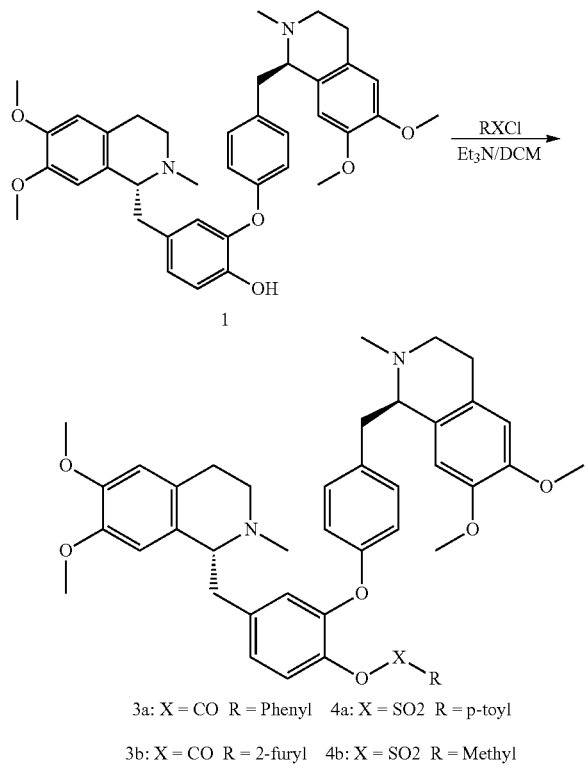

3a: X = CO  R = Phenyl    4a: X = SO2  R = p-toyl

3b: X = CO  R = 2-furyl    4b: X = SO2  R = Methyl

An equivalent of appropriate dauricine (20 mg, 0.032 mmol) was dissolved in dry dichloromethane (2 mL), and triethylamine (1.5 of equivalents) was added in one portion. Either carbonyl chloride or sulfonyl chloride (1.5 of equivalents) was subsequently added, and the mixture was stirred at room temperature for overnight. The reaction was monitored using TLC detection. The reaction mixture was quenched with water and extracted with dichloromethane. The dichloromethane extract was washed with brine, and then dried over MgSO$_4$. Finally, the solvent was evaporated and the residue was purified by column chromatography on silica gel to give light yellowish solid of compounds (3a, 3b, 4a and 4b).

Compound 3a: Purification by silica gel column chromatography (10:1 CHCl$_3$/MeOH) afforded 19.1 mg (82%) of 3a as light yellowish solid. TLC Rf=0.34 (10:1 CHCl$_3$/MeOH); Mp 103-105° C.; [α]$^{24}$D=-87.4° (c=0.2, MeOH); $^1$HNMR (600 MHz, CDCl$_3$): δ 8.09 (dd, J=1.8 Hz, 0.6 Hz, 1H), 7.59 (m, 1H), 7.45-7.47 (m, 2H), 7.17 (d, J=8.4 Hz, 1H), 7.01 (s, 1H), 7.00 (s, 1H), 6.94 (dd, J=8.4 Hz, 2.4 Hz, 1H), 6.85 (s, 1H), 6.83 (s, 1H), 6.78 (d, J=1.8 Hz, 1H), 6.56 (dd, J=3.6 Hz, 1.8 Hz, 1H), 6.55 (s, 1H), 6.12 (s, 1H), 5.99 (s, 1H), 3.85 (s, 3H), 3.84 (s, 3H), 3.68-3.74 (m, 2H), 3.70 (s, 3H), 3.46 (s, 3H), 3.19-3.23 (m, 2H), 3.17-3.18 (m, 1H), 3.15-3.16 (m, 1H), 2.83-2.87 (m, 2H), 2.75-2.82 (m, 4H), 2.57-2.62 (m, 2H), 2.53 (s, 3H), 2.52 (s, 3H). $^{13}$CNMR (150 MHz, CDCl$_3$): δ 164.7, 155.5, 148.2, 147.4, 147.3, 146.5, 146.3, 140.3, 139.1, 134.7, 133.5, 130.8, 130.2, 129.3, 128.9, 128.7, 128.5, 125.9, 125.7, 125.3, 123.2, 121.7, 117.9, 111.2, 111.2, 111.0, 110.8, 64.9, 64.6, 55.8, 55.8, 55.4, 46.8, 46.7, 42.6, 42.5, 40.6, 25.4, 25.2. HRMS (ESI): m/z for C$_{45}$H$_{48}$N$_2$O$_7$ calcd 728.3462, found 729.3527 [M+H]$^+$, 365.1800 [M+2H]$^{2+}$.

Compound 3b: Purification by silica gel column chromatography (10:1 CHCl$_3$/MeOH) afforded 19.6 mg (85%) of 3b as light yellowish solid. TLC Rf=0.33 (95:5 CHCl$_3$/MeOH); Mp 112-114° C.; [α]$^{24}$D=-97.8° (c=0.2, MeOH); $^1$HNMR (600 MHz, CDCl$_3$): δ 7.64 (dd, J=1.8 Hz, 0.6 Hz, 1H), 7.27 (dd, J=3.6 Hz, 0.6 Hz, 1H), 7.15 (d, J=7.8 Hz, 1H), 7.03 (s, 1H), 7.02 (s, 1H), 6.91 (dd, J=8.4 Hz, 2.4 Hz, 1H), 6.87 (s, 1H), 6.85 (s, 1H), 6.74 (d, J=1.8 Hz, 1H), 6.57 (s, 1H), 6.55 (dd, J=3.6 Hz, 1.8 Hz, 1H), 6.55 (s, 1H), 6.07 (s, 1H), 6.04 (s, 1H), 3.85 (s, 3H), 3.84 (s, 3H), 3.69-3.72 (m, 2H), 3.68 (s, 3H), 3.53 (s, 3H), 3.18-3.23 (m, 1H), 3.12-3.18 (m, 3H), 2.81-2.88 (m, 2H), 2.74-2.80 (m, 4H), 2.56-2.61 (m, 2H), 2.53 (s, 3H), 2.52 (s, 3H). $^{13}$CNMR (150 MHz, CDCl$_3$): δ 156.4, 155.2, 148.4, 147.3, 147.2, 147.9, 146.4, 146.3, 143.7, 139.4, 139.3, 135.0, 130.8, 129.1, 128.7, 125.9, 125.9, 125.1, 123.1, 121.5, 119.4, 118.2, 112.1, 111.2, 111.1, 111.0, 110.8, 64.8, 64.6, 55.8, 55.7, 55.5, 46.8, 46.7, 42.7, 42.6, 40.7, 25.5, 25.3. HRMS (ESI): m/z for C$_{43}$H$_{46}$N$_2$O$_8$ calcd 718.3254, found 719.3293 [M+H]$^+$, 360.1557 [M+2H]$^{2+}$.

Compound 4a: Purification by silica gel column chromatography (10:1 CHCl$_3$/MeOH) afforded 17.0 mg (74%) of 4a as light yellowish solid. TLC Rf=0.32 (10:1 CHCl$_3$/MeOH); Mp 117-119° C.; [α]$^{24}$D=-53.2° (c=0.2, MeOH); $^1$HNMR (600 MHz, CDCl$_3$): δ 7.71 (s, 1H), 7.70 (s, 1H), 7.24 (s, 1H), 7.23 (s, 1H), 7.15 (d, J=8.4 Hz, 1H), 6.97 (s, 1H), 6.96 (s, 1H), 6.82 (dd, J=8.4 Hz, 2.4 Hz, 1H), 6.56 (s, 1H), 6.54 (d, J=8.4 Hz, 1H), 6.53 (s, 1H), 6.52 (s, 1H), 6.49 (s, 1H), 6.08 (s, 1H), 6.05 (s, 1H), 3.84 (s, 3H), 3.80 (s, 3H), 3.68-3.70 (m, 1H), 3.63 (s, 3H), 3.62-3.63 (m, 1H), 3.58 (s, 3H), 2.99-3.21 (m, 4H), 2.65-2.80 (m, 6H), 2.55-2.59 (m, 1H), 2.52 (s, 3H), 2.46-2.51 (m, 1H), 2.45 (s, 3H), 2.41 (s, 3H). $^{13}$CNMR (150 MHz, CDCl$_3$): δ 154.5, 148.3, 147.3, 147.2, 146.5, 146.3, 145.0, 140.2, 138.3, 134.9, 133.1, 130.7, 129.5, 129.0, 128.6, 128.5, 126.3, 125.9, 124.9, 123.9, 121.3, 117.7, 111.1, 110.9, 110.6, 64.7, 64.3, 55.7, 55.6, 55.6, 47.1, 46.7, 42.6, 42.6, 40.6, 40.5, 25.6, 25.2, 21.6. HRMS (ESI): m/z for C$_{45}$H$_{50}$N$_2$O$_8$S calcd 778.3288, found 779.3325 [M+H]$^+$, 390.1715 [M+2H]$^{2+}$.

Compound 4b: Purification by silica gel column chromatography (10:1 CHCl$_3$/MeOH) afforded 20.0 mg (89%) of 4b as light yellowish solid. TLC Rf=0.32 (10:1 CHCl$_3$/MeOH); Mp 92-94° C.; [α]$^{24}$D=-82.7° (c=0.2, MeOH); $^1$HNMR (600 MHz, CDCl$_3$): δ 7.29 (d, J=8.4 Hz, 1H), 7.08 (s, 1H), 7.07 (s, 1H), 6.94 (dd, J=8.4 Hz, 1.8 Hz, 1H), 6.82 (s, 1H), 6.81 (s, 1H), 6.70 (d, J=2.4 Hz, 1H), 6.58 (s, 1H), 6.53 (s, 1H), 6.13 (s, 1H), 6.08 (s, 1H), 3.86 (s, 3H), 3.83 (s, 3H), 3.67-3.75 (m, 2H), 3.65 (s, 3H), 3.64 (s, 3H), 3.07-3.24 (m, 4H), 3.17 (s, 3H), 2.72-2.88 (m, 6H), 2.58-2.61 (m, 2H), 2.54 (s, 3H), 2.49 (s, 3H). 13CNMR (150 MHz, CDCl$_3$): δ 154.6, 148.0, 147.4, 147.3, 146.5, 146.5, 140.7, 138.5, 135.4, 131.1, 128.4, 126.2, 126.0, 125.5, 124.5, 121.8, 117.7, 111.2, 111.2, 110.9, 110.6, 64.7, 64.4, 55.8, 55.7, 55.7, 55.6, 46.8, 46.7, 42.6, 42.6, 40.6, 40.6, 25.3, 25.2.

HRMS (ESI): m/z for $C_{39}H_{46}N_2O_8S$ calcd 702.2975, found 703.3045 $[M+H]^+$, 352.1547 $[M+2H]^{2+}$.

Reagents, Chemicals, Antibodies and Plasmids for Biological Assay:

All chemicals and reagents were purchased from Sigma unless otherwise stated. The following regents were used: 3-methyladenine (Calbiochem, 189490), dauricine and N-desmethyldauricine (China Chengdu MUST). RIPA (radioimmunoprecipitation assay) lysis buffer (CST, 9806), antibodies against LC3B (CST, 2775) and anti-β-actin (Santa Cruz, sc-47778) were used.

Cell Culture:

All cells were obtained from the American Type Culture Collection (Rockville, Md., USA) unless otherwise specified. GFP-LC3 HeLa stable cells were kindly provided by Professor Li Min (School of Pharmaceutical Sciences, Sun-Yat-Sen University, Guangzhou, China). The flattened shape and discrete cellular compartments of HeLa cells provide morphological advantages for observing autophagosome formation. All media were supplemented with 10% fetal bovine serum and the antibiotics penicillin (50 U/ml) and streptomycin (50 μg/ml; Invitrogen, Paisley, Scotland, UK). All cell cultures were incubated at 37° C. in a 5% humidified $CO_2$ incubator.

Autophagy LC3 Puncta Detection:

The detection of LC3 autophagic puncta was conducted using GFP-LC3 stable HeLa cancer cells as described below. In brief, compounds-treated GFP-LC3-HeLa cells on cover slips were fixed with 4% paraformaldehyde (Sigma) for 20 min at room temperature and then rinsed with PBS (phosphate-buffered saline). The coverslips were then mounted with FLUORSAVE™ mounting media (Calbiochem, San Diego, Calif., USA) for fluorescence imaging and the localization of LC3 autophagosomes were captured under the API Delta Vision Live-cell Imaging System (Applied Precision Inc., GE Healthcare Company, Washington, USA). To quantify autophagy, guidelines were followed to monitor autophagy, the percentage of cells with punctuate LC3 immunofluorescence staining was calculated by counting the number of the cells showing the increased punctuate pattern of LC3 fluorescence (≥10 dots/cell) in immunofluorescence-positive cells over the total number of cells in the same field. A minimum of 1000 cells from randomly selected fields were scored.

Cytotoxicity Assays:

All test compounds were dissolved in DMSO (Dimethyl sulfoxide) at final concentrations of 50 mmol/L and stored at −20° C. before use. Cytotoxicity was assessed using the 3-(4, 5-dimethylthiazol-2-yl)-2, 5-diphenyltetrazolium bromide (MTT) (5.0 mg/ml) assay. Briefly, $4 \times 10^3$ cells were seeded per well in 96-well plates before drug treatment. After overnight culture, the cells were then exposed to different concentrations of test compounds (0.039-100 μmol/L) for 72 hours. Cells without drug treatment were used as control. Subsequently, MTT (10 μL) was added to each well and incubated at 37° C. for 4 hours followed by the addition of 100 μL solubilization buffer (10% SDS (Sodium dodecyl sulfate) in 0.01 mol/L HCl) and overnight incubation. A570 nm was determined from each well on the next day. The percentage of cell viability was calculated using the following formula: Cell viability (%)=$A_{treated}/A_{control} \times 100$. Data were obtained from triplication independent experiments.

Annexin V Detection by Flow Cytometry Analysis:

Apoptosis was detected by Annexin V staining kit (BD Biosciences, San Jose, Calif., USA). In brief, cells were exposed to the indicated concentrations of celastrol for 24 hours. Cells were then harvested and analyzed by flow cytometry using FITC-Annexin V and Propidium Iodide staining according to the manufacturer's instructions. Apoptotic cells were quantitatively counted by a flow cytometer (BD FACSAria III, San Jose, Calif., USA). Data acquisition and analysis were performed with CellQuest (BD Biosciences, San Jose, Calif., USA) from triple independent experiments.

Protein Extraction and Western Blotting:

After drug treatment, adherent and floating cells were lysed with RIPA lysis buffer. Protein concentrations were determined using the Bio-Rad protein assay (Bio-Rad Laboratories, Inc., Hercules, Calif., USA). The cell lysates of samples were subjected to electrophoresis on SDS polyacrylamide gels and transferred to Hybond enhanced chemiluminescence nitrocellulose membranes (Amersham Biosciences, Piscataway, N.J.), which were then blocked with 5% non-fat dry milk protein for 1 hour. Membranes were then incubated with the indicated primary antibodies overnight at 4° C. The binding of the antibody was visualized by peroxidase-coupled secondary antibody using the ECL (enhanced chemiluminescence) Western Blotting Detection Reagents (Invitrogen, Paisley, Scotland, UK). Band intensities were quantified by using the software ImageJ (NIH, Bethesda, Md., USA).

Statistical Analysis:

The results were expressed as means±S.D. as indicated. The difference was considered statistically significant when the p-value was less than 0.05. Student's t-test or one-way ANOVA analysis was used for comparison among different groups.

Example 2 Synthesis of Compounds

Compounds 2a, 2b, 2c, 2d, 2e, 2f, and 2g were synthesized as presented in Scheme 1. Briefly, dauricine reacted with commercially available carbamoyl chlorides at 0° C. in $CH_2Cl_2$ in the presence of $Et_3N$ to give seven carbamate compounds (2a-2g). Phenyl and alkyl chains such as methyl, ethyl, methoxyl or morpholinyl groups were introduced into dauricine to evaluate the role of different substituents on the N-termini of carbamates. The presence of barrier to rotation of the C—N bond in carbamate could give rise to two possible anti and syn stereoisomers. Doubling signals of syn and anti rotamers of compound 2d were observed in the $^{13}$C NMR spectrum due to the hindered rotation of C—N bond in the carbamate which results in two conformational stereoisomers.

Similarly, ester and sulfonate compounds 3a, 3b, 4a, and 4b were prepared as illustrated in Scheme 2 in order to compare the effects of different linking groups on autophagy activity. Dauricine was treated with $Et_3N$ at 0° C. in $CH_2Cl_2$, either carbonyl chloride or sulfonyl chloride was added dropwise at 0° C. The solution was then allowed to room temperature for overnight to afford aromatic carboxylic esters (compounds 3a and 3b), aromatic sulfonic ester (compound 4a) and methyl sulfonic ester (compound 4b).

Example 3 Effect of Compounds in the Cytotoxicity and Autophagy in Cancer Cells

FIG. 1 is a graph 100 showing cell viability of HeLa cells treated with dauricine, N-desmethyldauricine, and compounds 2a-4b. HeLa cancer cells in 96 well-plates were treated with 0 to 20 μM of dauricine (Dau), N-desmethyldauricine (NDau) and dauricine derivatives (2a-4b) for 72 hours. Cell cytotoxicity was then assessed using the 3-(4, 5-dimethylthiazol-2-yl)-2, 5-diphenyltetrazolium bromide (MTT) (5.0 mg/ml) assay. The $IC_{50}$ values shown in FIG. 1 are mean values of three independent experiments.

Dauricine as a direct AMPK activator, activates autophagy and autophagic cell death in HeLa cancer cells via AMPK-mTOR signaling pathways. The derivative of dauricine, N-desmethyldauricine, was identified as autophagy inducer. N-desmethyldauricine targets sarcoplasmic reticulum $Ca^{2+}$ ATPase (SERCA) for calcium mobilization and thereby induces autophagic cell death in apoptosis-defective cancer. The anti-cancer effect of compounds 2a-2g, and 3a-4b via autophagy induction was investigated. The cytotoxicity of dauricine, N-desmethyldauricine and compounds 2a-4b in HeLa cancer cells are compared. As shown in FIG. 1, dauricine and N-desmethyldauricine exhibited potent anti-cancer effect with $IC_{50}$ at 15.53 and 15.80 µM respectively. Compounds 2a, 2b, 3a, and 4a exhibited stronger cytotoxic effect in cancer cells with mean $IC_{50}$ at 5.44 µM, 6.72 µM, 6.44 µM, 6.10 µM, respectively. Compounds 2c, 2d, 2e, 2f, 2g, 3b, and 4b exhibited cytotoxic effect in cancer cells with $IC_{50}$ more than 20 µM.

FIG. 2A-3H show identification of compounds 2a-4b with autophagic activities. GFP-LC3 puncta in compound-treated GFP-LC3-HeLa cells were detected. GFP-LC3 stable HeLa cells were treated with DMSO (−ve Ctrl) or the indicated concentrations of dauricine (Dau), N-desmethyldauricine (NDau) and dauricine derivatives (2a-4b) for 24 hours. Representative fluorescence images from the highest tested concentration of compound captured at 60× magnification were shown; scale bar, 15 µm. Bar charts represent the quantitation of autophagic cells. The percentages of autophagic cells were calculated as the number of cells with GFP-LC3 puncta (≥10 puncta/cell) divided by the total number of GFP-positive cells in the same field.

Figure 2C:
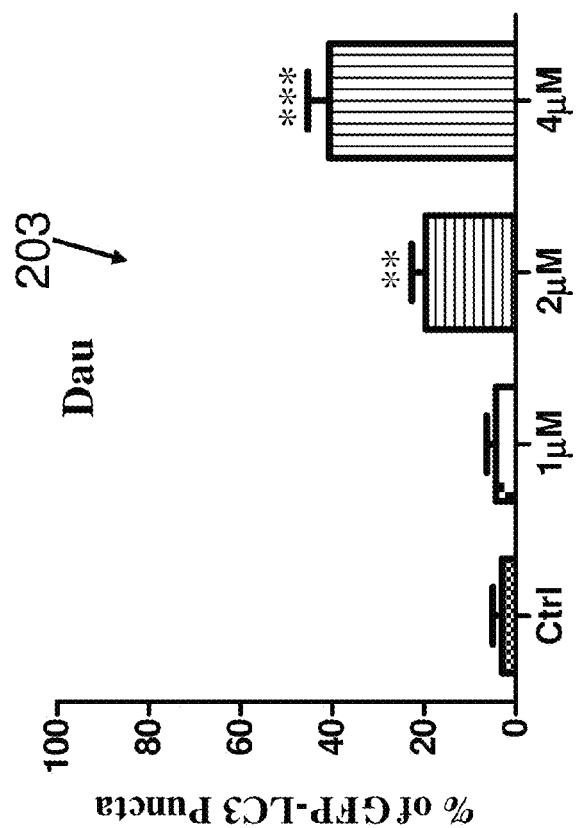
FIG. 2C shows a graph illustrating the percentage of GFP-LC3 puncta in HeLa cells treated with dauricine at concentrations of 0, 1, 2, and 4 µM in accordance with an example embodiment.
Figure 2B:
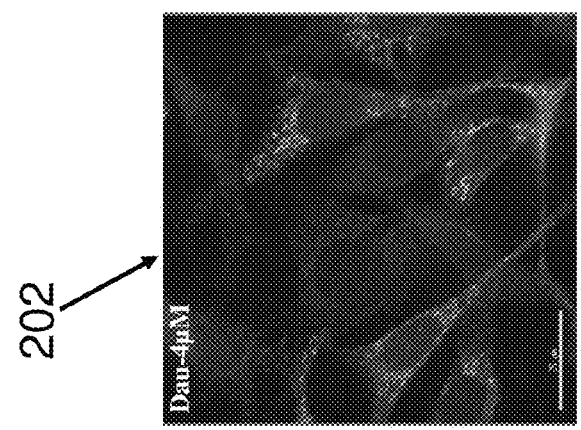
FIG. 2B shows autophagic activities of HeLa cells treated with dauricine (Dau) at the concentration of 4 µM in accordance with an example embodiment.
Figure 2A:
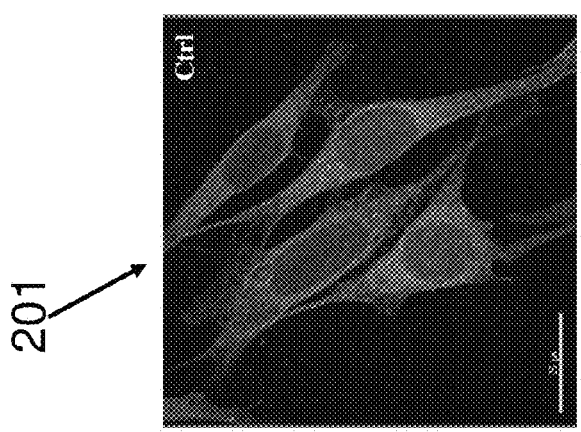
FIG. 2A shows autophagic activities of HeLa cells treated with Dimethyl sulfoxide (DMSO) (Ctrl) in accordance with an example embodiment.
Figure 2E:
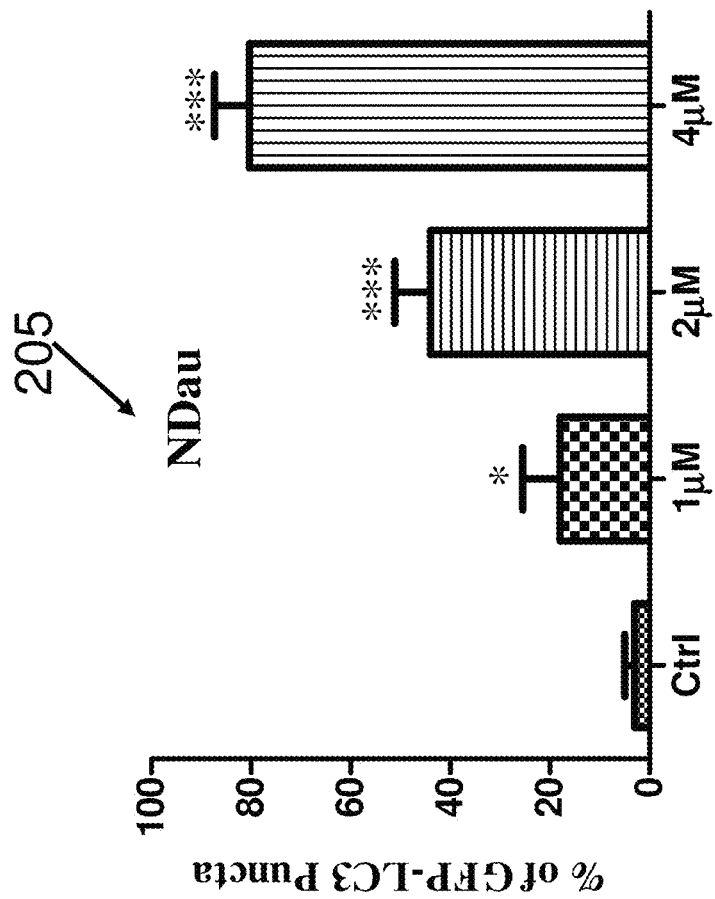
FIG. 2E shows a graph illustrating the percentage of GFP-LC3 puncta in HeLa cells treated with NDau at concentrations of 0, 1, 2, and 4 µM in accordance with an example embodiment.
Figure 2D:
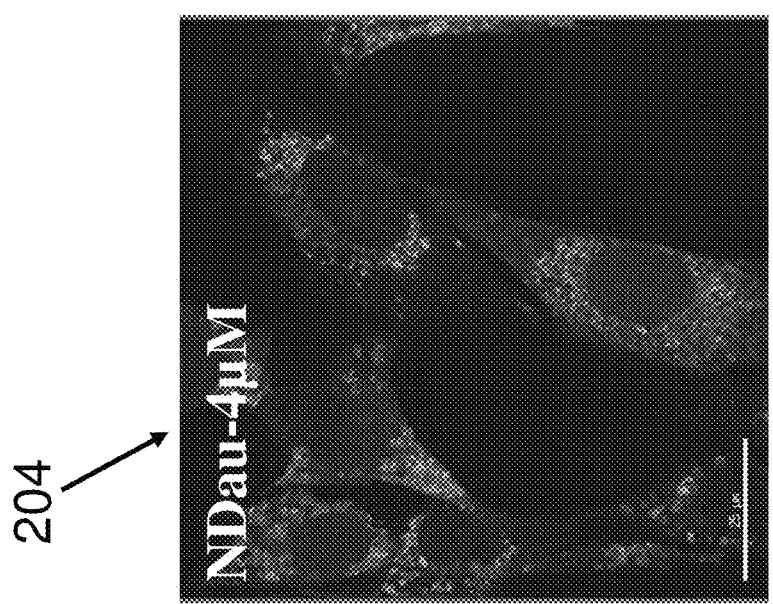
FIG. 2D shows autophagic activities of HeLa cells treated with N-desmethyldauricine (NDau) at the concentration of 4 µM in accordance with an example embodiment.
Figure 2G:
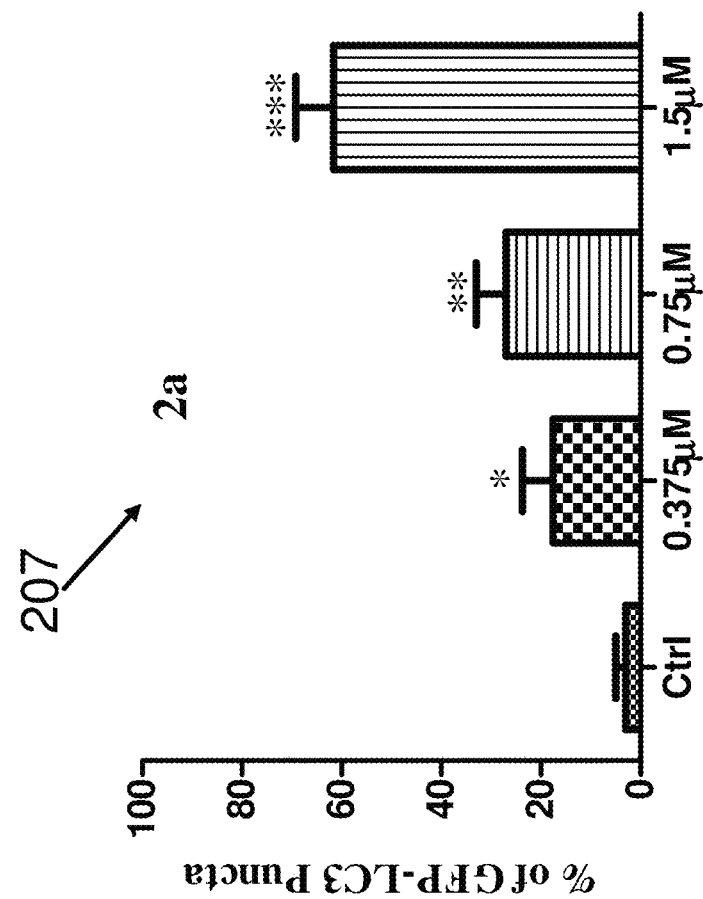
FIG. 2G shows a graph illustrating the percentage of GFP-LC3 puncta in HeLa cells treated with compound 2a at concentrations of 0, 0.375, 0.75, and 1.5 µM in accordance with an example embodiment.
Figure 2F:
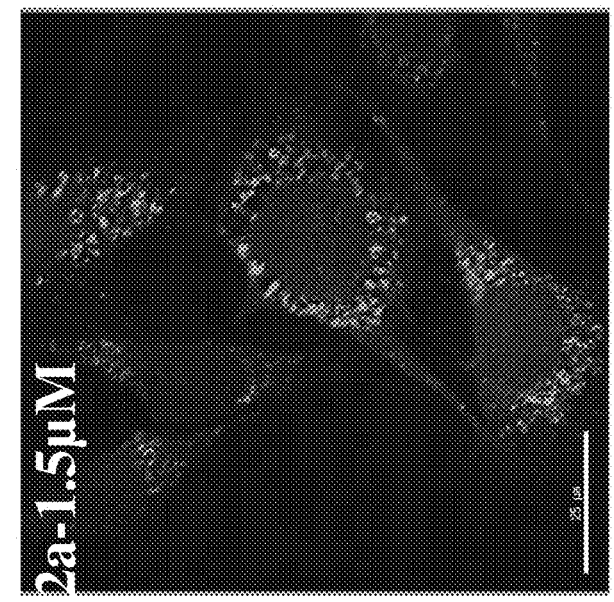
FIG. 2F shows autophagic activities of HeLa cells treated with compound 2a at the concentration of 1.5 µM in accordance with an example embodiment.
Figure 2I:
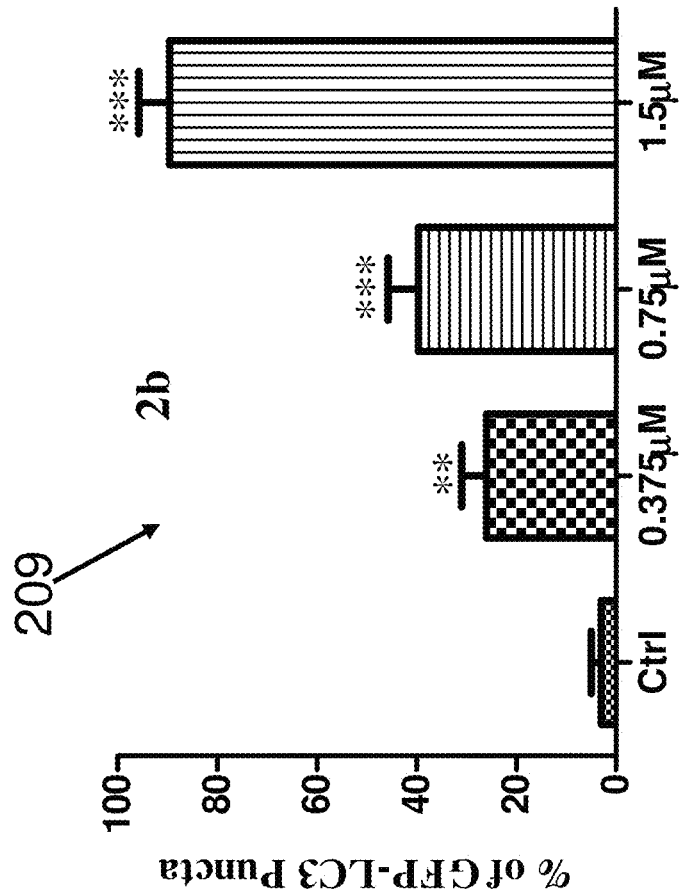
FIG. 2I shows a graph illustrating the percentage of GFP-LC3 puncta in HeLa cells treated with compound 2b at concentrations of 0, 0.375, 0.75, and 1.5 µM in accordance with an example embodiment.
Figure 2H:
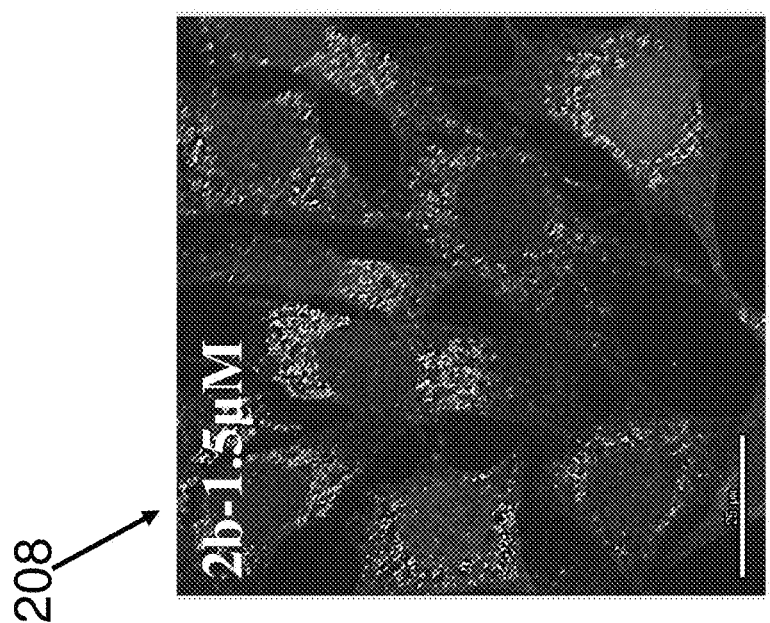
FIG. 2H shows autophagic activities of HeLa cells treated with compound 2b at the concentration of 1.5 µM in accordance with an example embodiment.
Figure 2K:
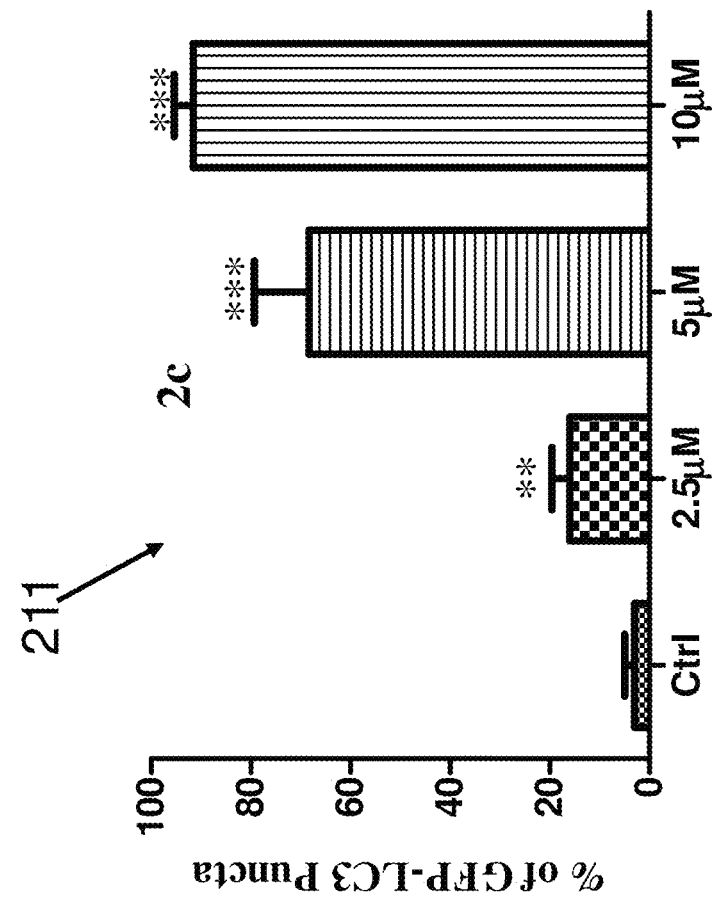
FIG. 2K shows a graph illustrating the percentage of GFP-LC3 puncta in HeLa cells treated with compound 2c at concentrations of 0, 2.5, 5, and 10 µM in accordance with an example embodiment.
Figure 2J:
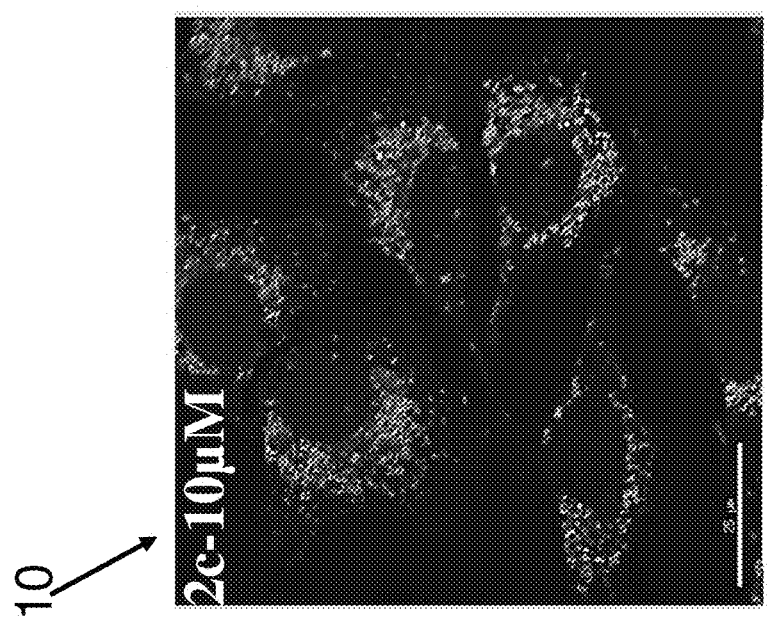
FIG. 2J shows autophagic activities of HeLa cells treated with compound 2c at the concentration of 10 µM in accordance with an example embodiment.
Figure 2M:
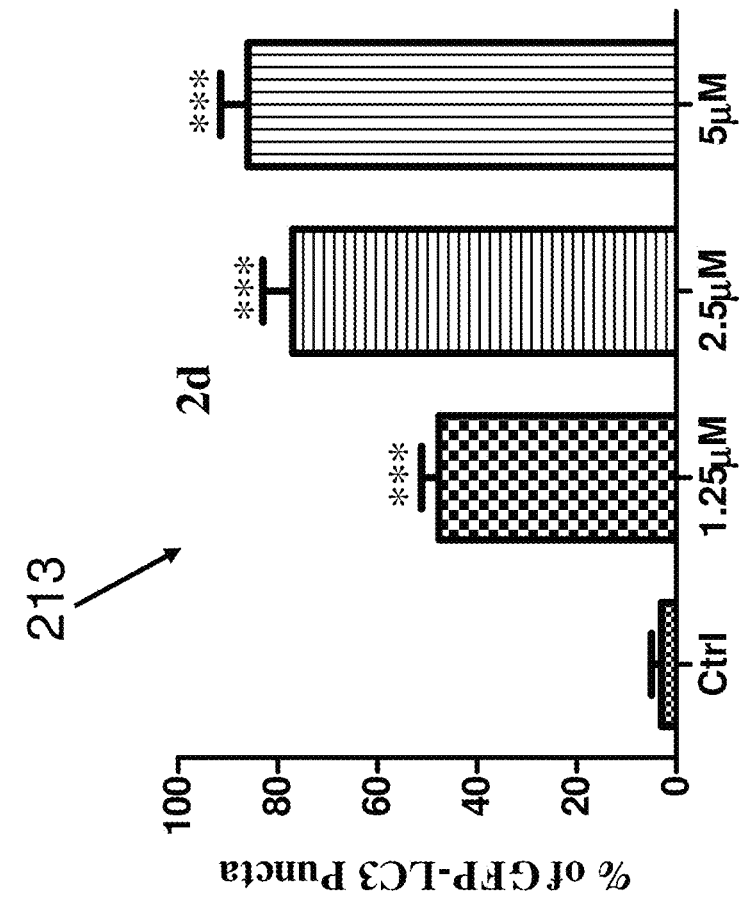
FIG. 2M shows a graph illustrating the percentage of GFP-LC3 puncta in HeLa cells treated with compound 2d at concentrations of 0, 1.25, 2.5, and 5 µM in accordance with an example embodiment.
Figure 2L:
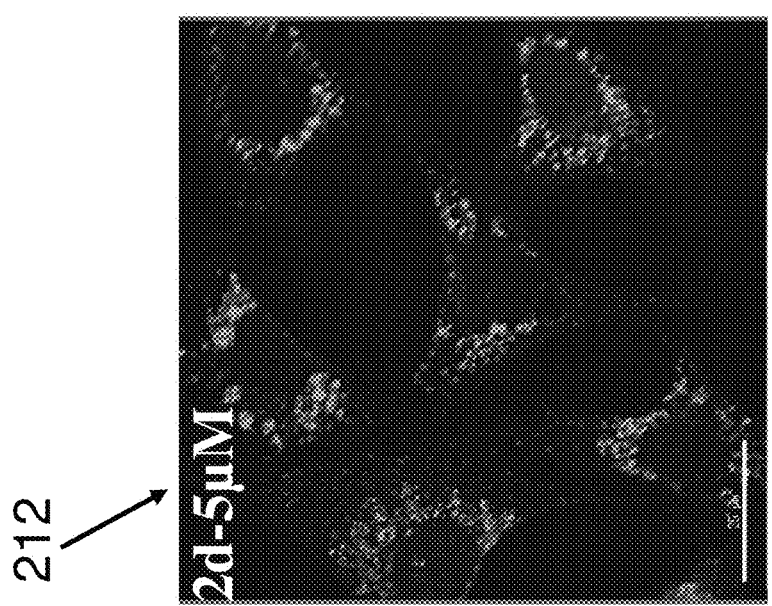
FIG. 2L shows autophagic activities of HeLa cells treated with compound 2d at the concentration of 5 µM in accordance with an example embodiment.
Figure 2O:
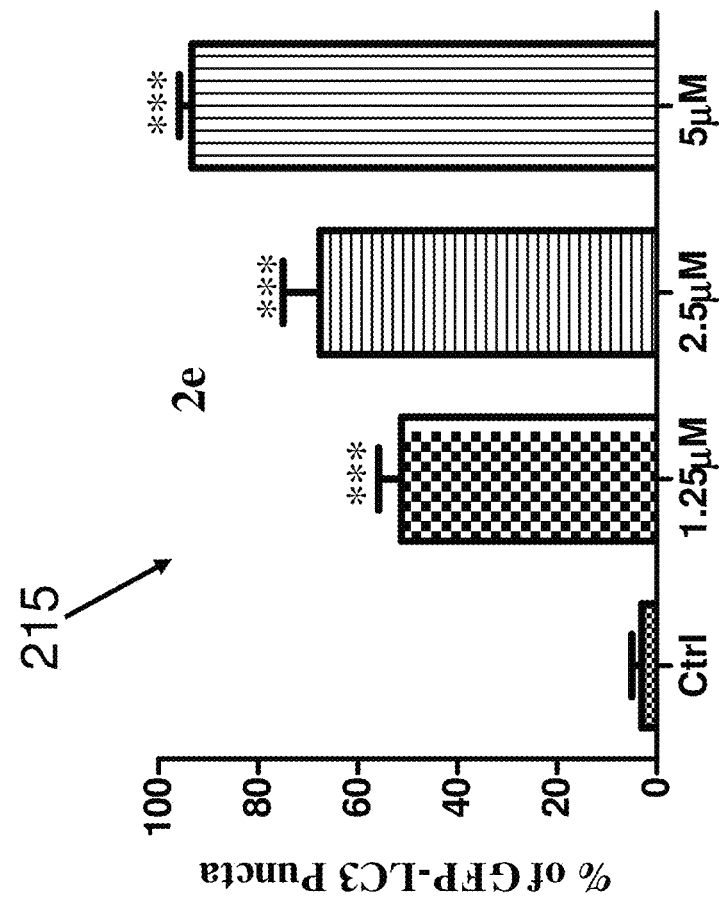
FIG. 2O shows a graph illustrating the percentage of GFP-LC3 puncta in HeLa cells treated with compound 2e at concentrations of 0, 1.25, 2.5, and 5 µM in accordance with an example embodiment.
Figure 2N:
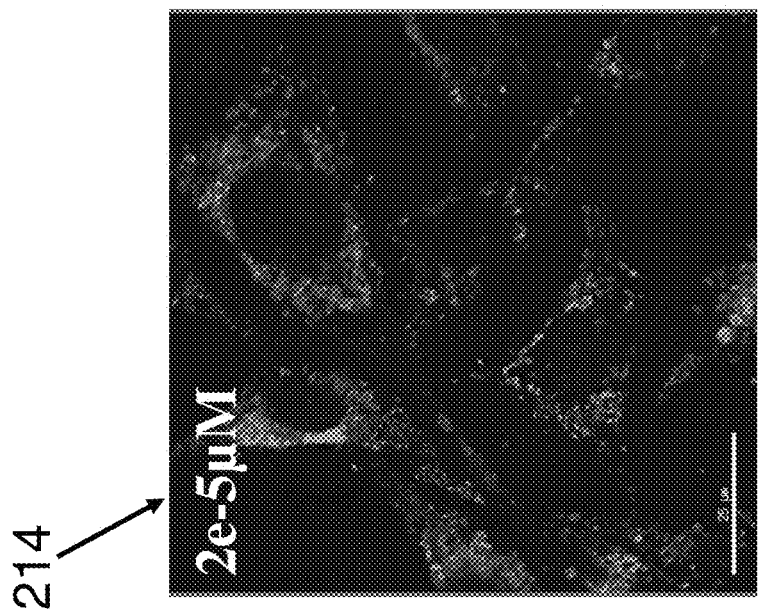
FIG. 2N shows autophagic activities of HeLa cells treated with compound 2e at the concentration of 5 µM in accordance with an example embodiment.
Figure 2Q:
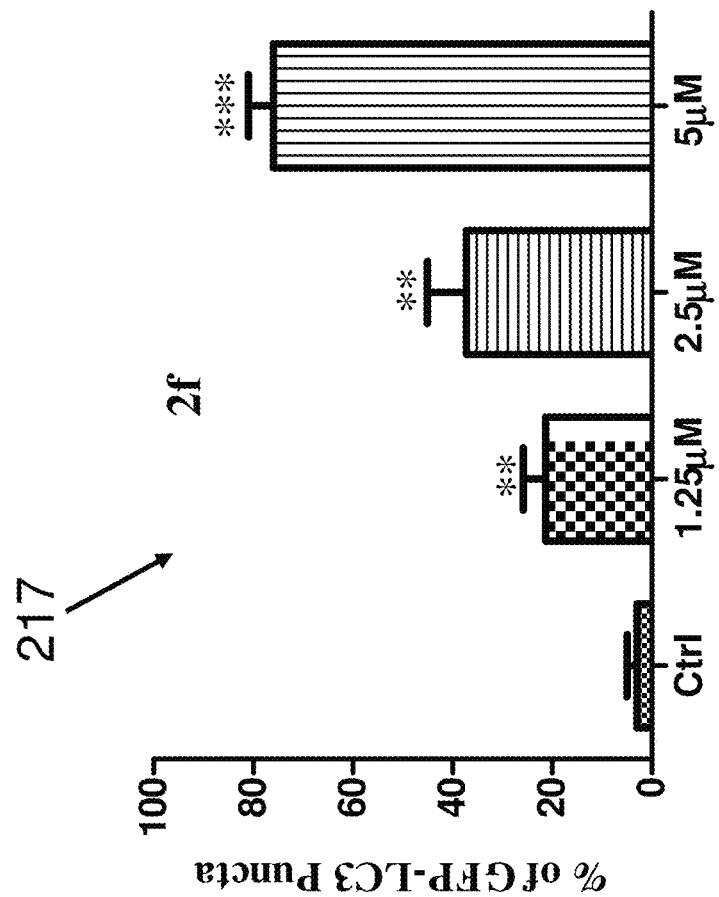
FIG. 2Q shows a graph illustrating the percentage of GFP-LC3 puncta in HeLa cells treated with compound 2f at concentrations of 0, 1.25, 2.5, and 5 µM in accordance with an example embodiment.
Figure 2P:
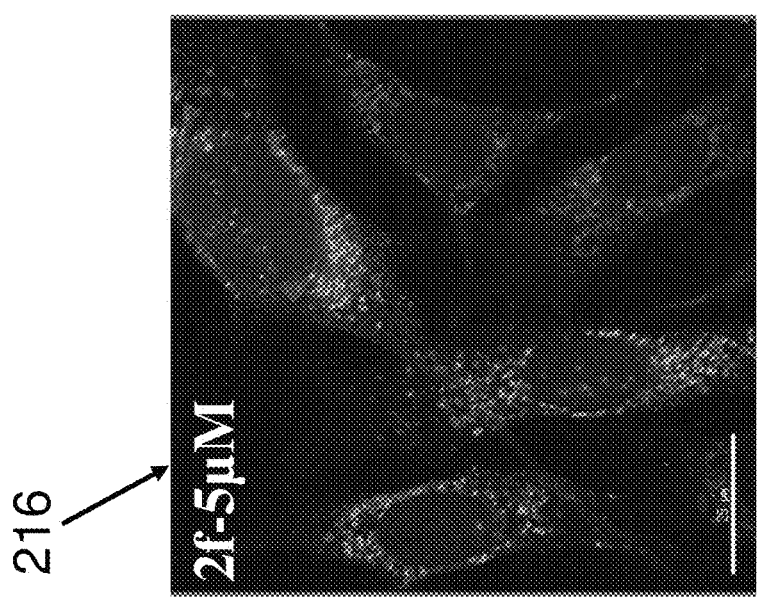
FIG. 2P shows autophagic activities of HeLa cells treated with compound 2f at the concentration of 5 µM in accordance with an example embodiment.
Figure 2S:
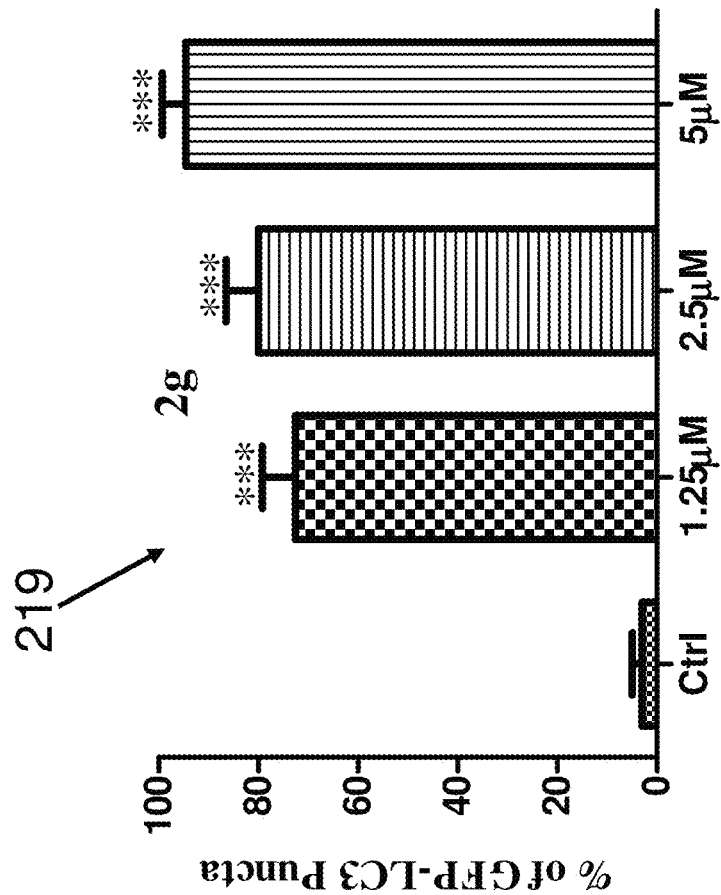
FIG. 2S shows a graph illustrating the percentage of GFP-LC3 puncta in HeLa cells treated with compound 2g at concentrations of 0, 1.25, 2.5, and 5 µM in accordance with an example embodiment.
Figure 2R:
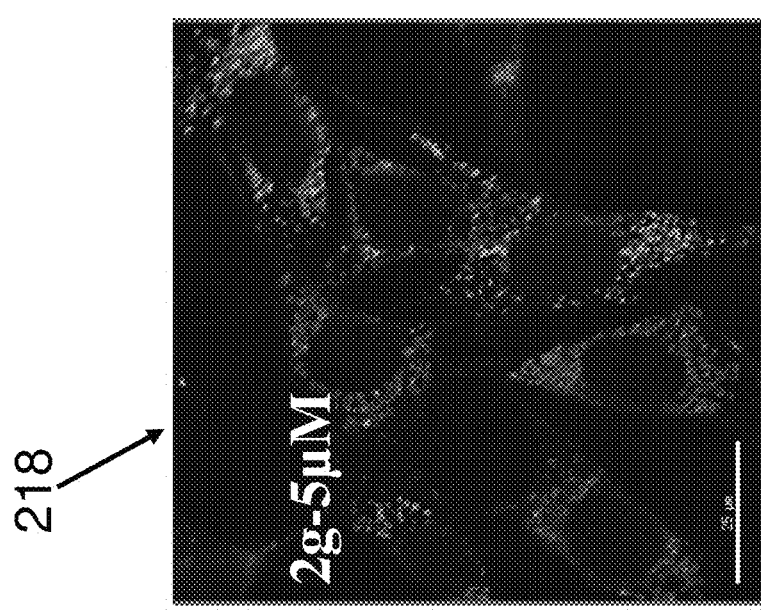
FIG. 2R shows autophagic activities of HeLa cells treated with compound 2g at the concentration of 5 µM in accordance with an example embodiment.
Figure 3D:
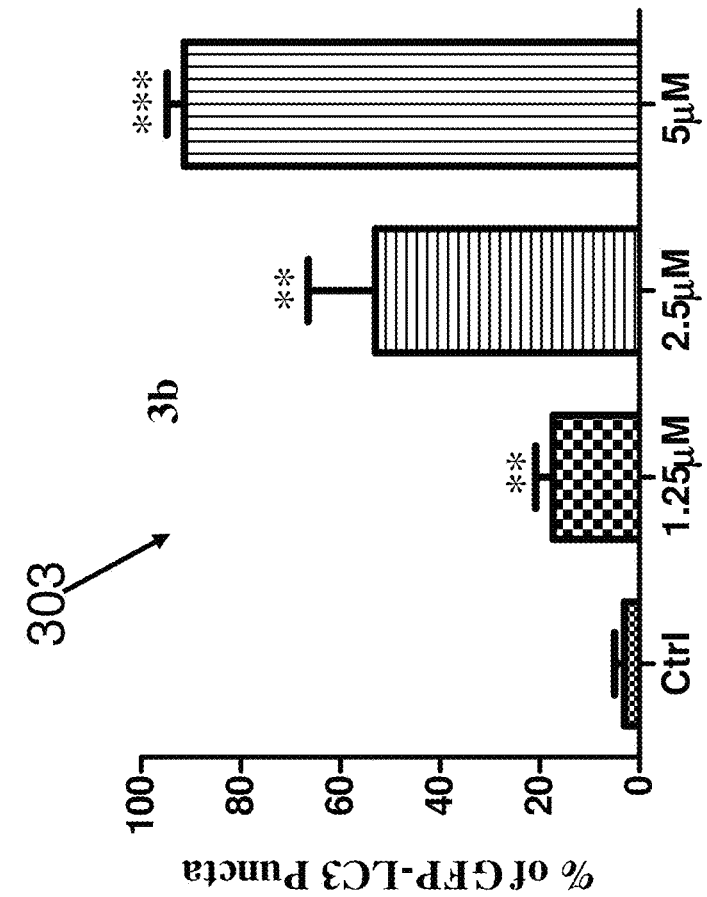
FIG. 3D shows a graph illustrating the percentage of GFP-LC3 puncta in HeLa cells treated with compound 3b at concentrations of 0, 1.25, 2.5, and 5 µM in accordance with an example embodiment.
Figure 3C:
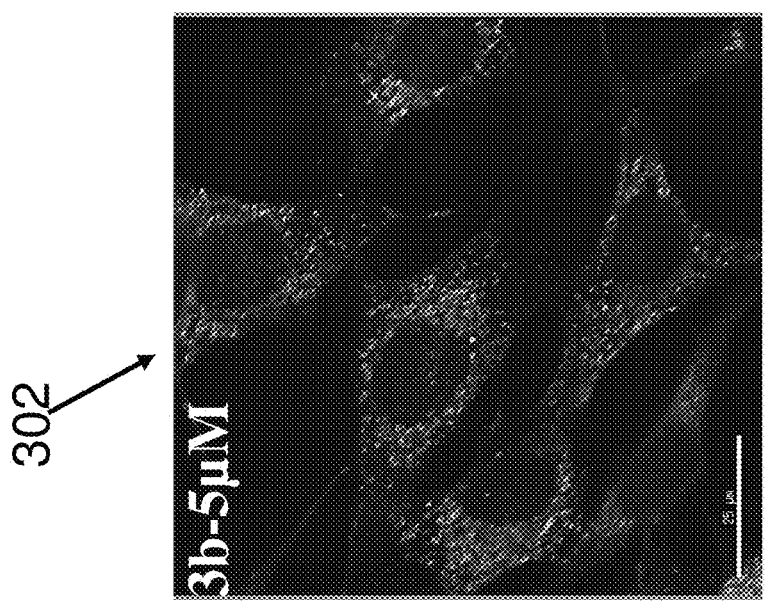
FIG. 3C shows autophagic activities of HeLa cells treated with compound 3b at the concentration of 5 µM in accordance with an example embodiment.
Figures 3E, 3F:
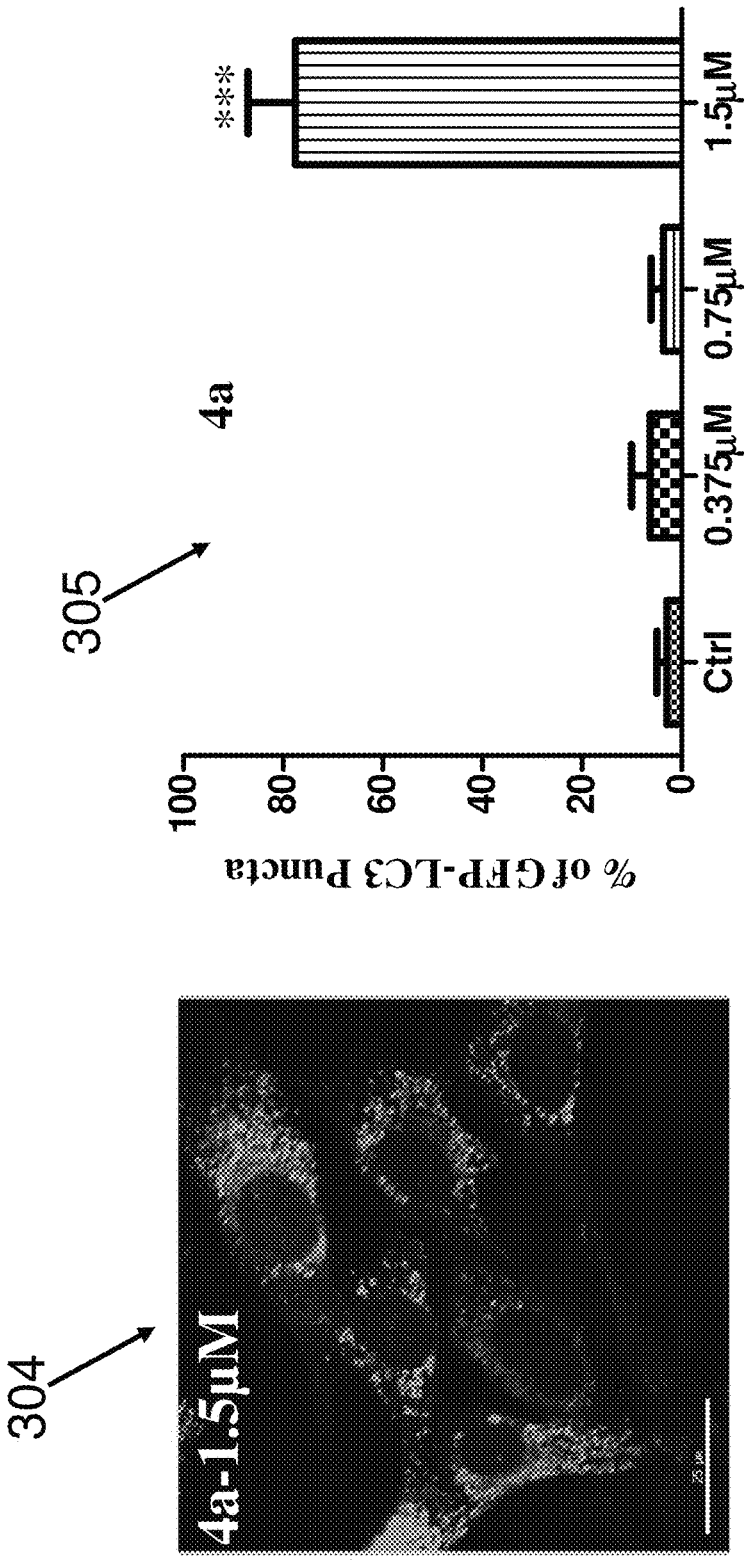
FIG. 3E shows autophagic activities of HeLa cells treated with compound 4a at the concentration of 1.5 µM in accordance with an example embodiment.
FIG. 3F shows a graph illustrating the percentage of GFP-LC3 puncta in HeLa cells treated with compound 4a at concentrations of 0, 0.375, 0.75, and 1.5 µM in accordance with an example embodiment.
Figure 3H:
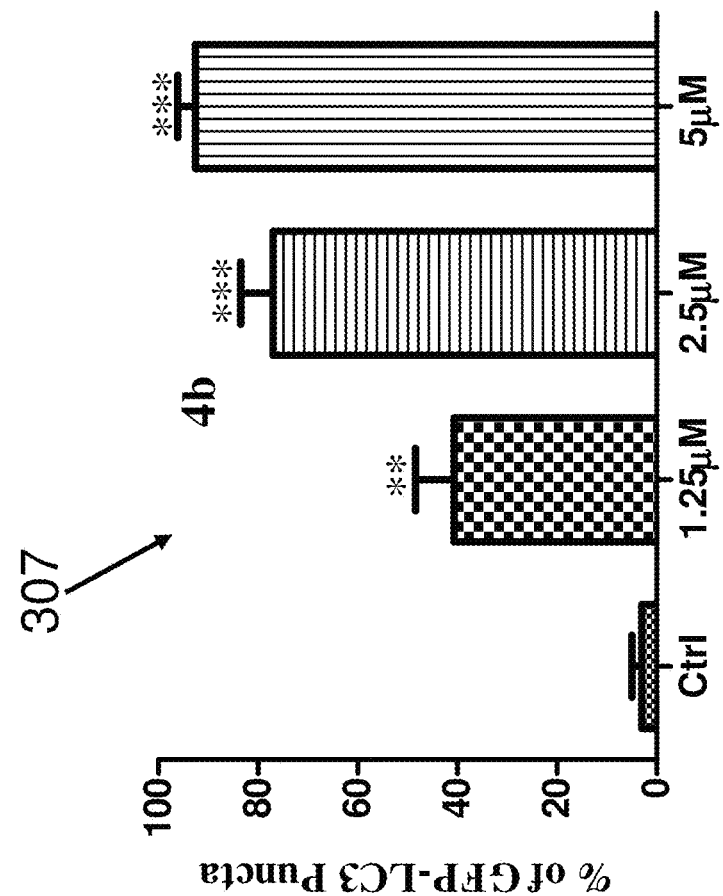
FIG. 3H shows a graph illustrating the percentage of GFP-LC3 puncta in HeLa cells treated with compound 4b at concentrations of 0, 1.25, 2.5, and 5 µM in accordance with an example embodiment.
Figure 3G:
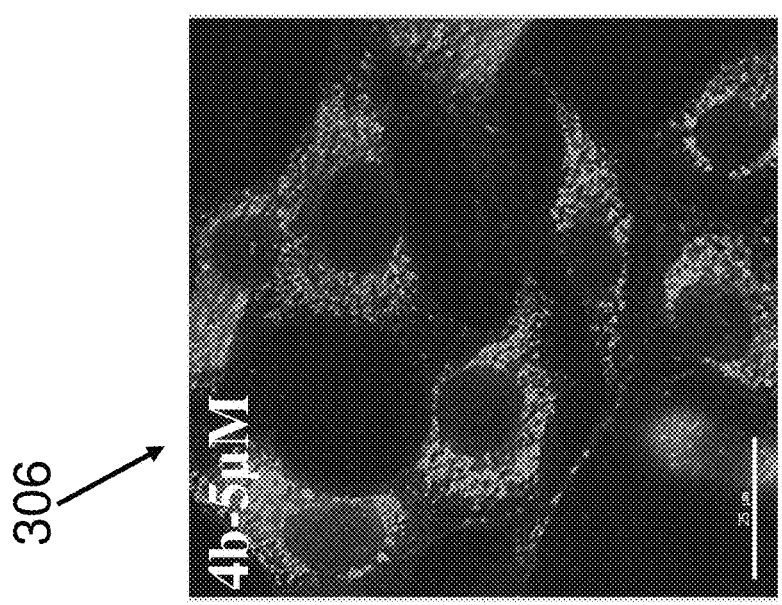
FIG. 3G shows autophagic activities of HeLa cells treated with compound 4b at the concentration of 5 µM in accordance with an example embodiment.

FIG. 2A is a drawing 201 showing the conversion of cytosolic LC3-I to membrane-bound LC3-II in untreated HeLa cells. FIG. 2B is a drawing 202 showing the conversion of cytosolic LC3-I to membrane-bound LC3-II in HeLa cells treated with 4 µM of dauricine. FIG. 2C is a graph 203 showing the percentage of GFP-LC3 puncta in HeLa cells treated with dauricine at concentrations of 0, 1, 2, and 4 µM. FIG. 2D is a drawing 204 showing the conversion of cytosolic LC3-I to membrane-bound LC3-II in HeLa cells treated with 4 µM of N-desmethyldauricine. FIG. 2E is a graph 205 showing the percentage of GFP-LC3 puncta in HeLa cells treated with N-desmethyldauricine at concentrations of 0, 1, 2, and 4 µM.

The conversion of cytosolic LC3-I to membrane-bound LC3-II, an essential step for the induction of autophagy, was monitored in GFP-LC3 stable expressing HeLa cancer cells. As shown in FIGS. 2A-2B and 2D, untreated control cells indicated no green fluorescence puncta formation, whereas dauricine and N-desmethyldauricine had increased formation of GFP-LC3 puncta in HeLa cells. Dauricine and N-desmethyldauricine induced autophagic puncta in HeLa cells in a dose-dependent manner (FIGS. 2C and 2E).

FIGS. 2F, 2H, 2J, 2L, 2N, 2P, 2R, 3A, 3C, 3E, 3G show drawings 206, 208, 210, 212, 214, 216, 218, 300, 302, 304, and 306 illustrating the conversion of LC3-I to LC3-II in HeLa cells treated with compounds 2a, 2b, 2c, 2d, 2e, 2f, 2g, 3a, 3b, 4a, and 4b, respectively. FIGS. 2G, 2I, 2K, 2M, 2O, 2Q, 2S, 3B, 3D, 3F, 3H are graphs 207, 209, 211, 213, 215, 217, 219, 301, 303, 305, 307 showing the percentage of GFP-LC3 puncta in HeLa cells treated with compounds 2a-4b, respectively.

Compounds 2a-4b (11 compounds) had increased formation of GFP-LC3 puncta in HeLa cells, compared with untreated cells (FIGS. 2F, 2H, 2J, 2L, 2N, 2P, 2R, 3A, 3C, 3E, 3G). Compounds 2a-4b induced autophagic puncta in HeLa cells in a dose-dependent manner as shown in FIGS. 2G, 2I, 2K, 2M, 2O, 2Q, 2S, 3B, 3D, 3F, 3H. It shows that compounds 2a-4b can activate autophagy in the cancer cells.

The presence of the autophagy marker protein, LC3-II was determined in HeLa cells by western blot analysis. HeLa cancer cells were treated with dauricine (Dau) or compounds 2a-4b with three indicated concentrations for 24 hours. Cell lysates were analyzed by Western blot for LC3 conversion (LC3-I, 18 kDa; LC3-II, 16 kDa) and β-actin. The western blot was shown in FIGS. 4A, 4C, 4E, 4G, 4I, 4K, and 4M. LC3-II band intensities were quantified using densitometric analysis and normalised to β-actin. The results were shown in FIGS. 4B, 4D, 4F, 4H, 4J, 4L and 4N. Data are expressed as a fold change relative to the DMSO-treated negative control. Bars are representatives of three independent experiments. Error bars, SEM. *, P<0.05; , P<0.01; *, P<0.001.

Figures 4A, 4B:
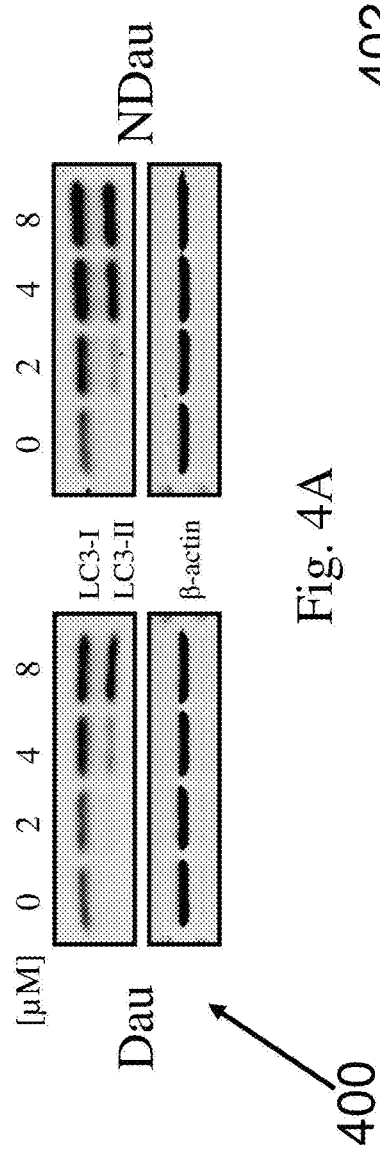
FIG. 4A shows the western blot analysis on the autophagic marker LC3 conversion in HeLa cells treated with Dau and NDau at concentrations of 0, 2, 4, and 8 µM in accordance with an example embodiment.
FIG. 4B shows a quantitative graph for the western blot analysis of FIG. 4A illustrating the fold change of LC3 conversion in HeLa cells treated with Dau and NDau at concentrations of 0, 2, 4, and 8 µM in accordance with an example embodiment.

FIG. 4A shows the western blot analysis 400 for the autophagic marker LC3 conversion in HeLa cells treated with dauricine and N-desmethyldauricine at concentrations of 0, 2, 4, and 8 µM. FIG. 4B is a graph 402 showing the quantitative analysis for the LC3 conversion in HeLa cells treated with dauricine and N-desmethyldauricine at concentrations of 0, 2, 4, and 8 µM. The results show that Dauricine and N-desmethyldauricine increased the conversion of LC3-I to LC3-II in a dose-dependent manner.

FIG. 4C shows the western blot analysis 404 for the autophagic marker LC3 conversion in HeLa cells treated with compounds 2a and 2b at concentrations of 0, 0.75, 1.5, and 3 µM. FIG. 4D is a graph 406 showing the quantitative analysis for the LC3 conversion in HeLa cells treated with compounds 2a and 2b at concentrations of 0, 0.75, 1.5, and 3 µM. The results show that compounds 2a and 2b increased the conversion of LC3-I to LC3-II in a dose dependent manner, similar as dauricine and N-desmethyldauricine.

Figure 4E:
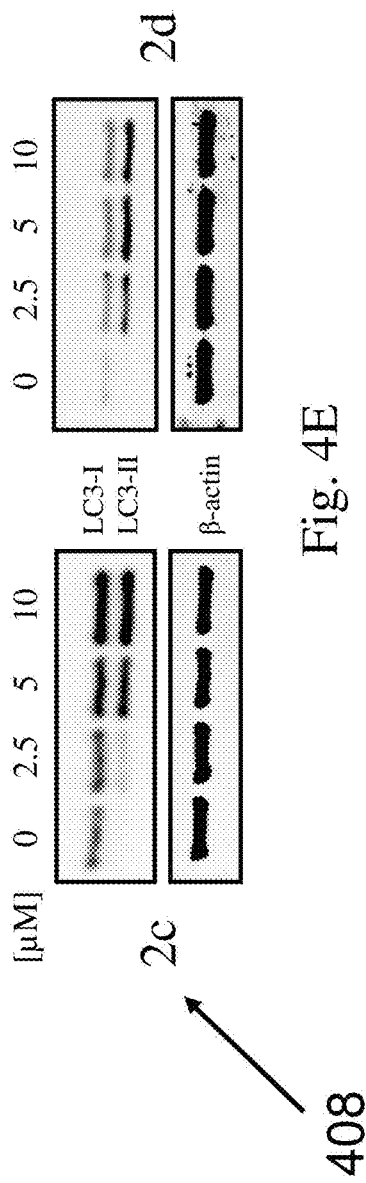
FIG. 4E shows the western blot analysis on the autophagic marker LC3 conversion in HeLa cells treated with compounds 2c and 2d at concentrations of 0, 2.5, 5, and 10 µM in accordance with an example embodiment.
Figure 4F:
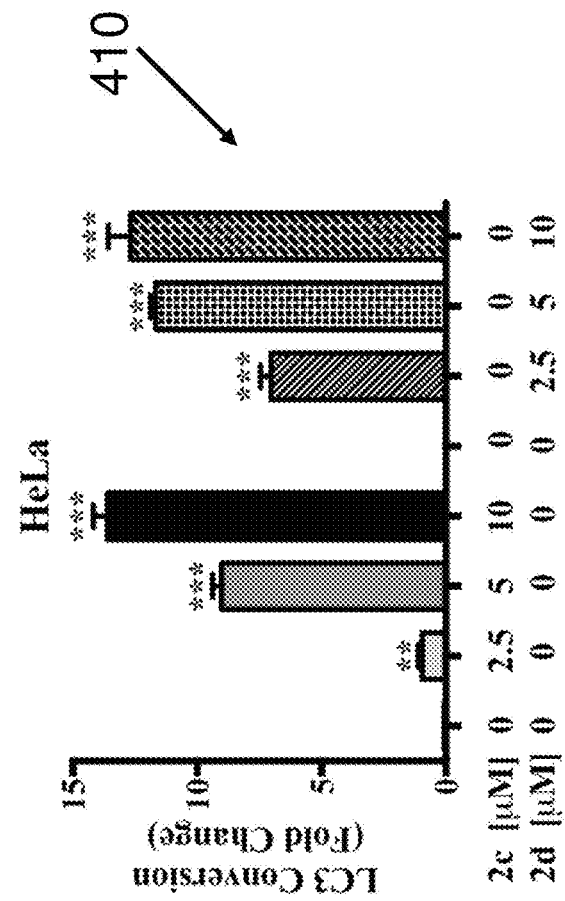
FIG. 4F shows a quantitative graph for the western blot analysis of FIG. 4E illustrating the fold change of LC3 conversion in HeLa cells treated with compounds 2c and 2d at concentrations of 0, 2.5, 5, and 10 µM in accordance with an example embodiment.

FIG. 4E shows the western blot analysis 408 for the autophagic marker LC3 conversion in HeLa cells treated with compounds 2c and 2d at concentrations of 0, 2.5, 5, and 10 µM. FIG. 4F is a graph 410 showing the quantitative analysis for the LC3 conversion in HeLa cells treated with compounds 2c and 2d at concentrations of 0, 2.5, 5, and 10 µM. The results show that compounds 2c and 2d increased the conversion of LC3-I to LC3-II in a dose dependent manner, similar as dauricine and N-desmethyldauricine.

Figure 4G:
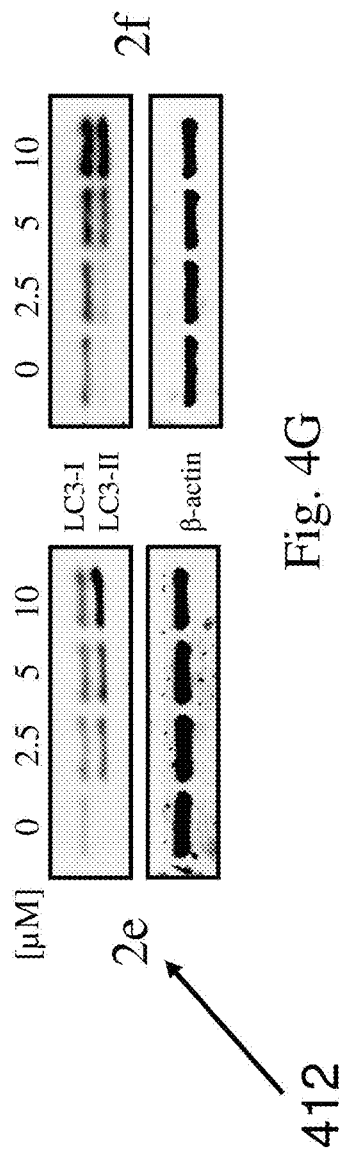
FIG. 4G shows the western blot analysis on the autophagic marker LC3 conversion in HeLa cells treated with compounds 2e and 2f at concentrations of 0, 2.5, 5, and 10 µM in accordance with an example embodiment.
Figure 4H:
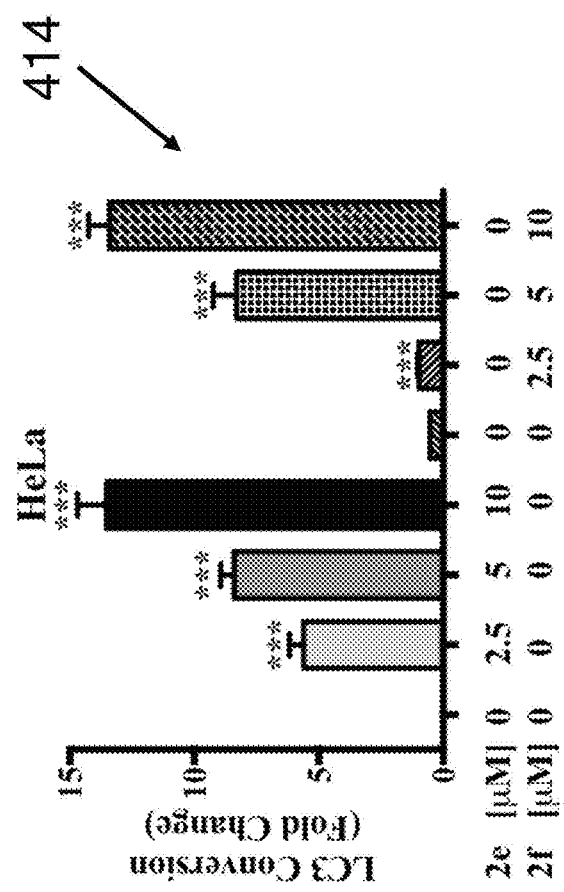
FIG. 4H shows a quantitative graph for the western blot analysis of FIG. 4G illustrating the fold change of LC3 conversion in HeLa cells treated with compounds 2e and 2f at concentrations of 0, 2.5, 5, and 10 µM in accordance with an example embodiment.

FIG. 4G shows the western blot analysis 412 for the autophagic marker LC3 conversion in HeLa cells treated with compounds 2e and 2f at concentrations of 0, 2.5, 5, and 10 µM. FIG. 4H is a graph 414 showing the quantitative analysis for the LC3 conversion in HeLa cells treated with compounds 2e and 2f at concentrations of 0, 2.5, 5, and 10 µM. The results show that compounds 2e and 2f increased the conversion of LC3-I to LC3-II in a dose dependent manner, similar as dauricine and N-desmethyldauricine.

Figure 4I:
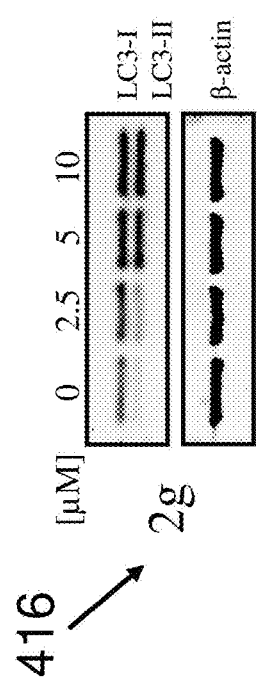
FIG. 4I shows the western blot analysis on the autophagic marker LC3 conversion in HeLa cells treated with compound 2g at concentrations of 0, 2.5, 5, and 10 µM in accordance with an example embodiment.
Figure 4J:
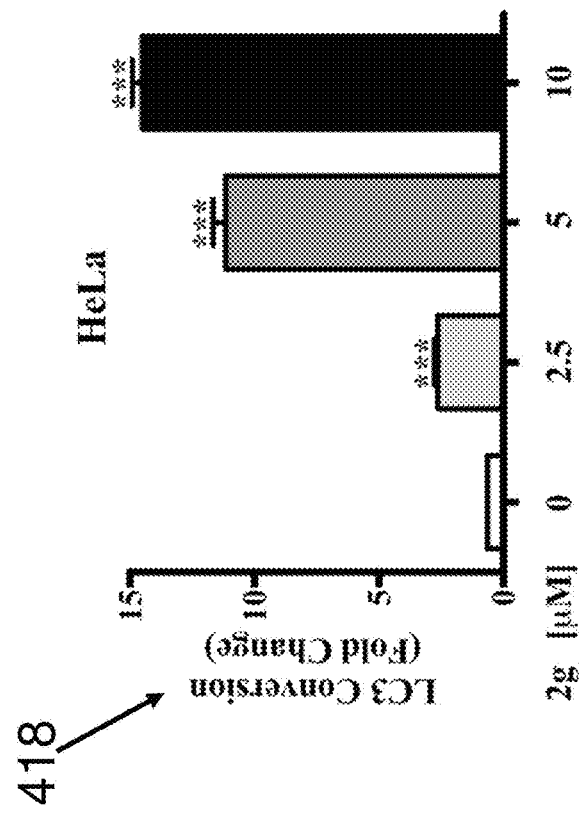
FIG. 4J shows a quantitative graph for the western blot analysis of FIG. 4I illustrating the fold change of LC3 conversion in HeLa cells treated with compound 2g at concentrations of 0, 2.5, 5, and 10 µM in accordance with an example embodiment.

FIG. 4I shows the western blot analysis 416 for the autophagic marker LC3 conversion in HeLa cells treated with compound 2g at concentrations of 0, 2.5, 5, and 10 µM. FIG. 4J is a graph 418 showing the quantitative analysis for the LC3 conversion in HeLa cells treated with compound 2g at concentrations of 0, 2.5, 5, and 10 µM. The results show that compound 2g increased the conversion of LC3-I to LC3-II in a dose dependent manner, similar as dauricine and N-desmethyldauricine.

Figure 4K:
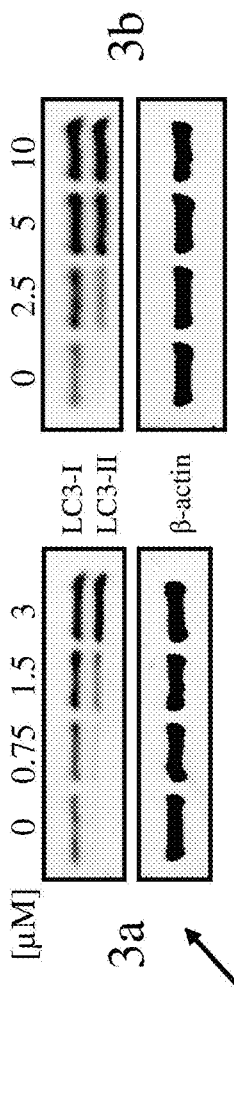
FIG. 4K shows the western blot analysis on the autophagic marker LC3 conversion in HeLa cells treated with compound 3a at concentrations of 0, 0.75, 1.5, and 3 µM and compound 3b at concentrations of 0, 2.5, 5, and 10 µM in accordance with an example embodiment.
Figure 4L:
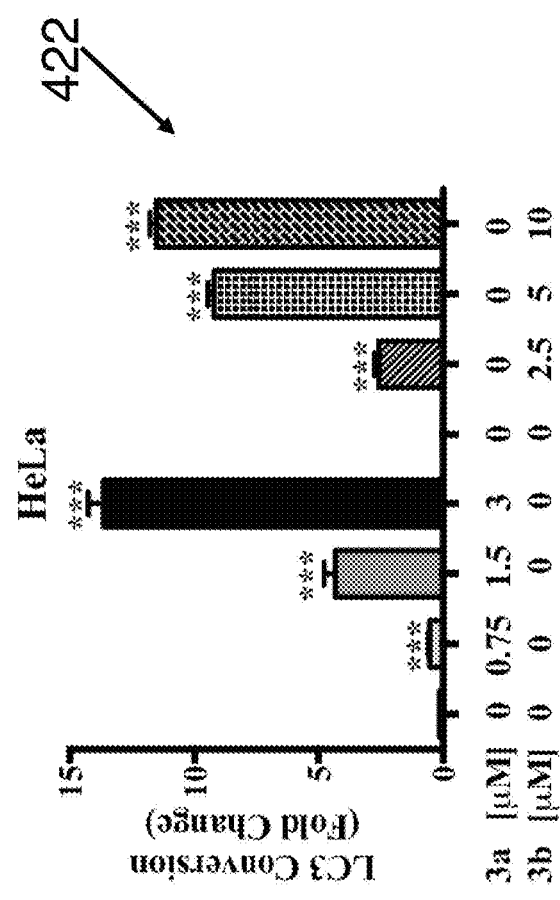
FIG. 4L shows a quantitative graph for the western blot analysis of FIG. 4K illustrating the fold change of LC3 conversion in HeLa cells treated with compound 3a at concentrations of 0, 0.75, 1.5, and 3 µM and compound 3b at concentrations of 0, 2.5, 5, and 10 µM in accordance with an example embodiment.

FIG. 4K shows the western blot analysis 420 for the autophagic marker LC3 conversion in HeLa cells treated with compound 3a at concentrations of 0, 0.75, 1.5, and 3 µM and compound 3b at concentrations of 0, 2.5, 5, and 10

μM. FIG. 4L is a graph 422 showing the quantitative analysis for the LC3 conversion in HeLa cells treated with compound 3a at concentrations of 0, 0.75, 1.5, and 3 μM and compound 3b at concentrations of 0, 2.5, 5, and 10 μM. The results show that compounds 3a and 3b increased the conversion of LC3-I to LC3-II in a dose dependent manner, similar as dauricine and N-desmethyldauricine.

Figure 4M:
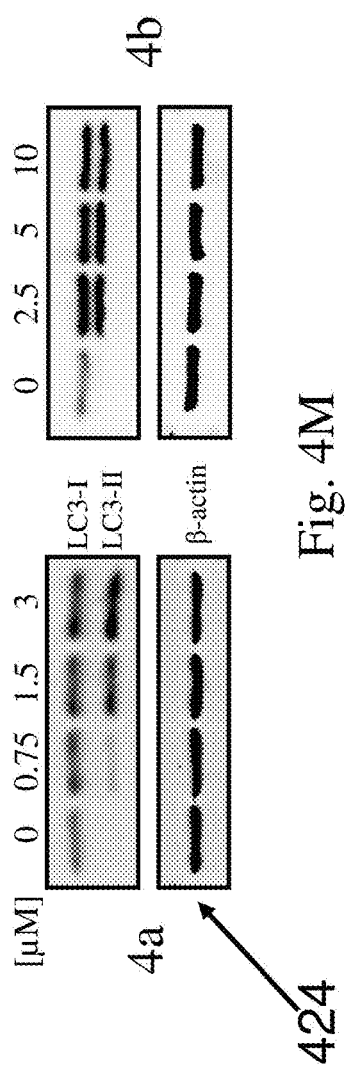
FIG. 4M shows the western blot analysis on the autophagic marker LC3 conversion in HeLa cells treated with compounds 4a and 4b at concentrations of 0, 0.75, 1.5, and 3 µM in accordance with an example embodiment.
Figure 4N:
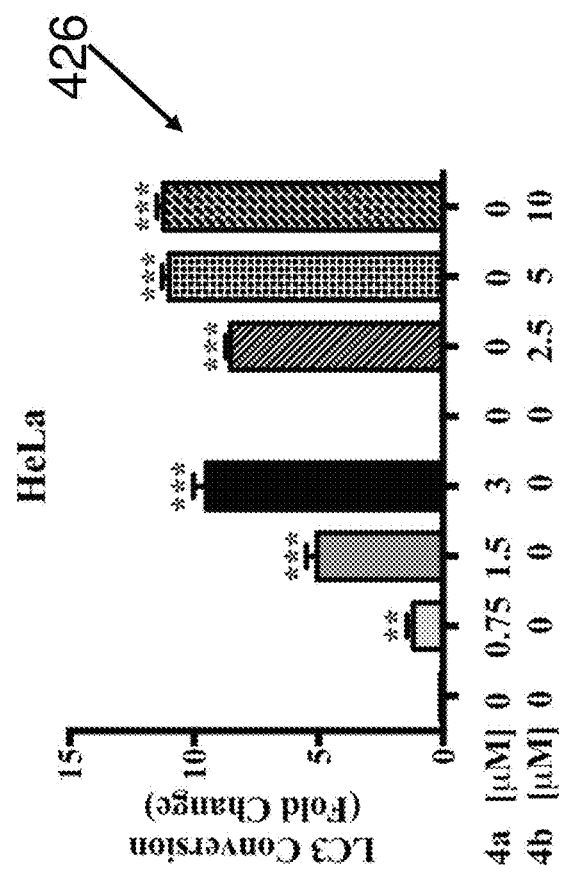
FIG. 4N shows a quantitative graph for the western blot analysis of FIG. 4M illustrating the fold change of LC3 conversion in HeLa cells treated with compounds 4a and 4b at concentrations of 0, 0.75, 1.5, and 3 µM in accordance with an example embodiment.

FIG. 4M shows the western blot analysis 424 for the autophagic marker LC3 conversion in HeLa cells treated with compound 4a at concentrations of 0, 0.75, 1.5, and 3 μM and compound 4b at concentrations of 0, 2.5, 5, and 10 μM. FIG. 4N is a graph 426 showing the quantitative analysis for the LC3 conversion in HeLa cells treated with compound 4a at concentrations of 0, 0.75, 1.5, and 3 μM and compound 4b at concentrations of 0, 2.5, 5, and 10 μM. The results show that compounds 4a and 4b increased the conversion of LC3-I to LC3-II in a dose dependent manner, similar as dauricine and N-desmethyldauricine.

These results indicate that compounds 2a-4b can induce autophagy in Hela cancer cells.

Example 4 Effect of Compounds 2a, 2b, 3a and 4a in Inducing Autophagic Cell Death in Cancer Cells To investigate whether the autophagy induced by compounds 2a, 2b, 3a, and 4a contributes to cell death, Annexin V cell death analysis was conducted. HeLa cells treated with these compounds (5 μM) in the presence or absence of 1 μM of wortmannin for 24 hours were assayed by flow cytometry after annexin V staining. The flow cytometry analysis was shown in FIGS. 5A, 5B and 5D. Bar charts of FIGS. 5C and 5E represent the quantitation of cell death (%).

Figure 5A:
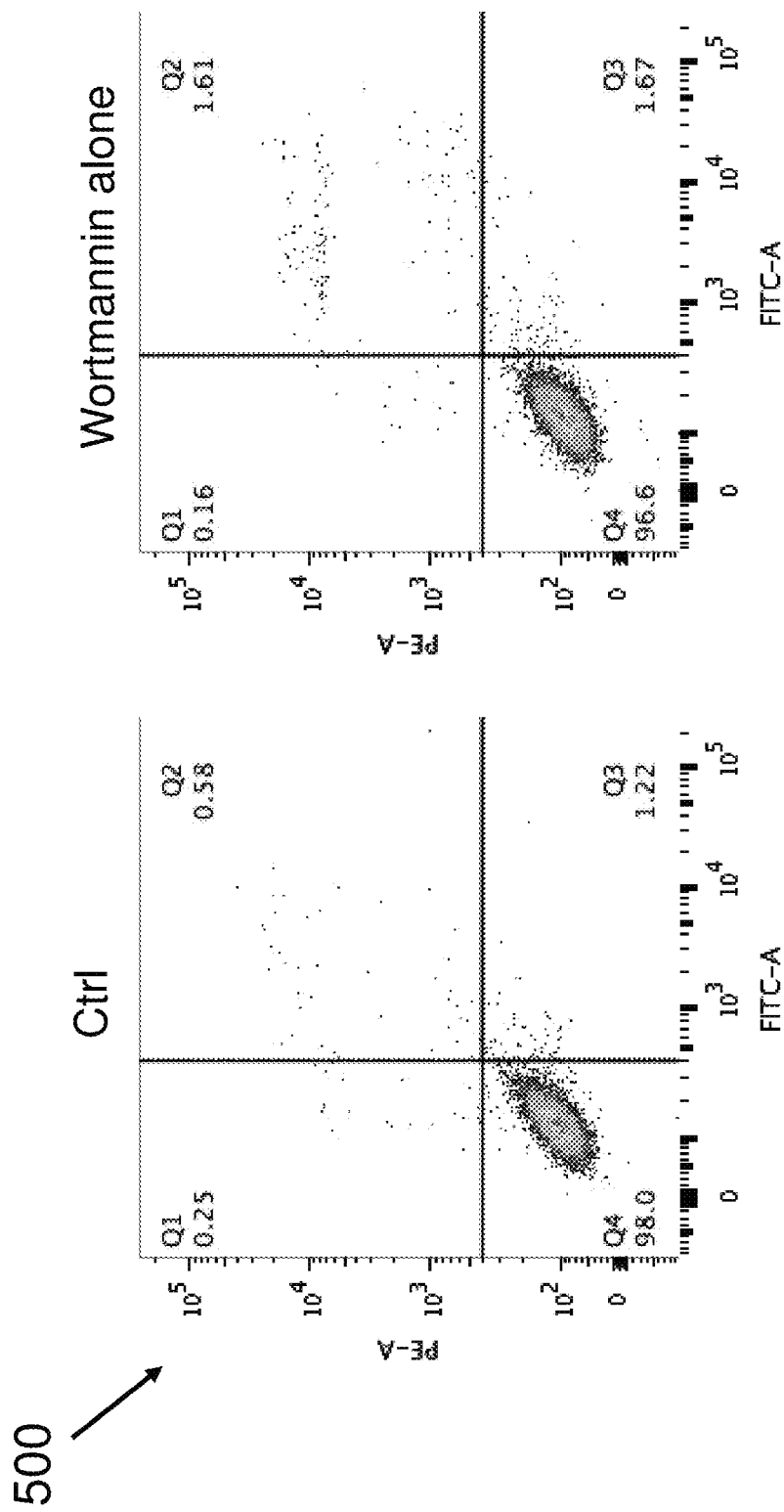
FIG. 5A and FIG. 5B show the flow cytometry analysis for HeLa cells treated with DMSO (Ctrl), Wortmannin alone, compounds 2a and 2b together with Wortmannin or without Wortmannin in accordance with an example embodiment.
Figure 5B:
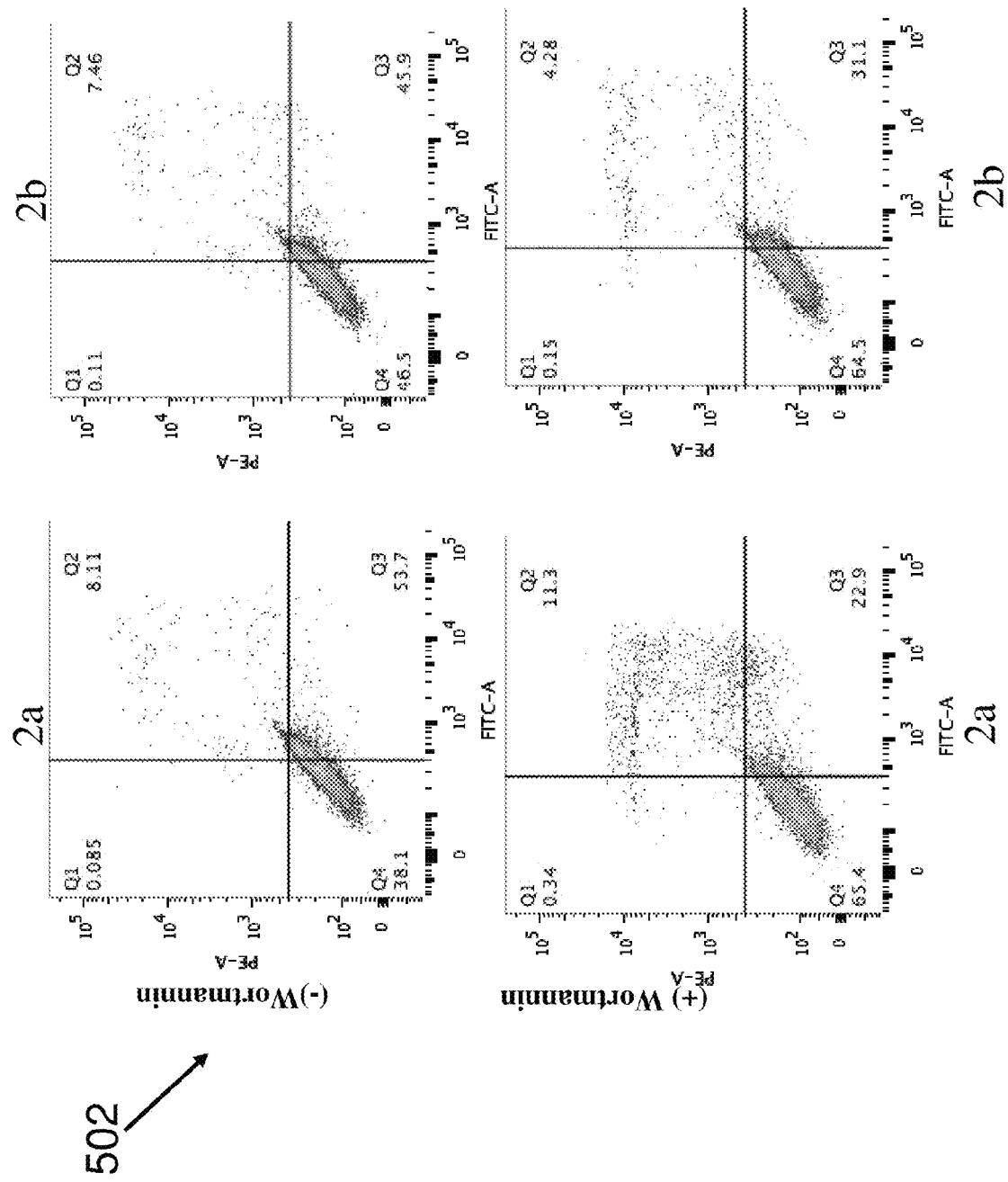
Figure 5C:
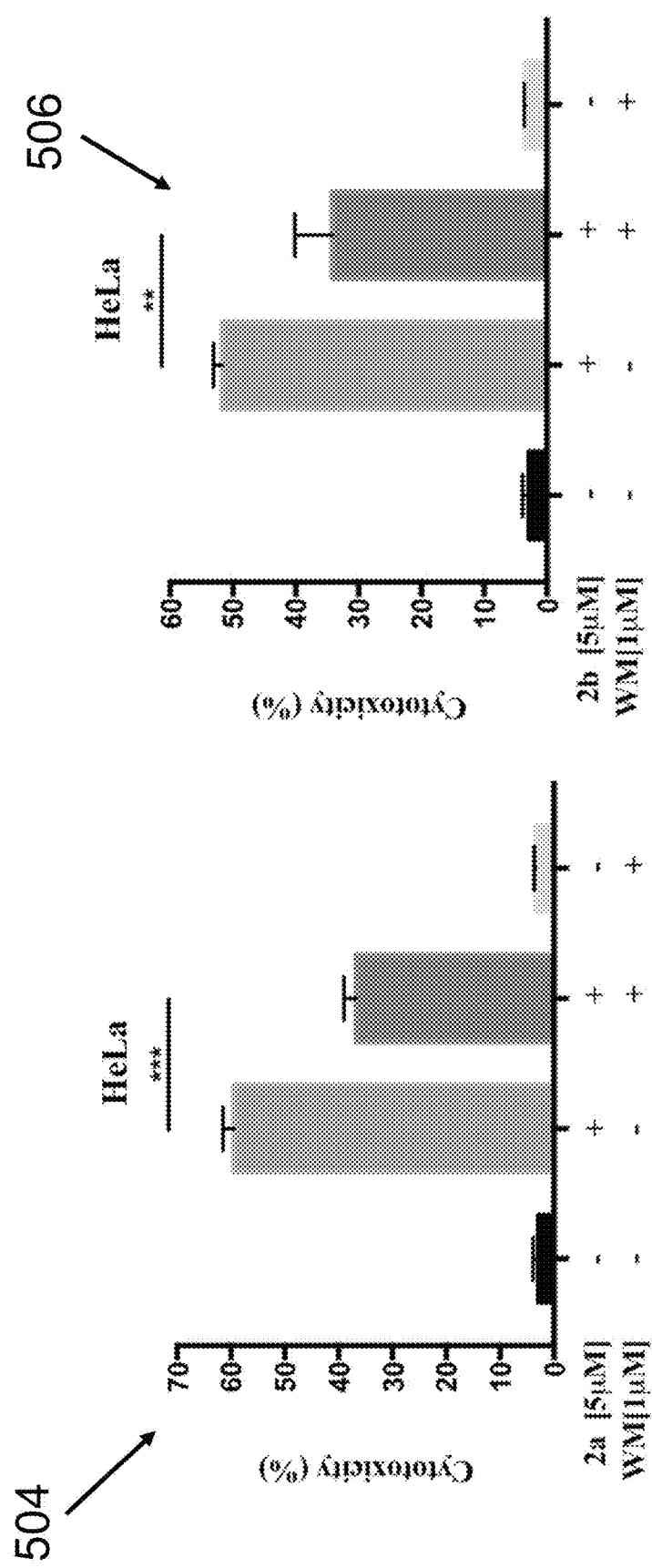
FIG. 5C shows a quantitative graph for the flow cytometry analysis of FIGS. 5A and 5B illustrating the cytotoxicity of compounds 2a and 2b in HeLa cells in accordance with an example embodiment.

FIG. 5A and FIG. 5B show the flow cytometry analysis 500 and 502 for HeLa cells treated with DMSO (Ctrl), Wortmannin alone (WM, autophagy inhibitor), compounds 2a and 2b together with Wortmannin or without Wortmannin. FIG. 5C shows graphs 504 and 506 illustrating the quantitative analysis for the flow cytometry analysis.

As shown in FIG. 5A, DMSO treatment control and wortmannin (WM) exhibited no cytotoxic effect in HeLa cancer cells. As shown in FIGS. 5B and 5C, compounds 2a and 2b markedly increased the percentage of cell death, and blocking of autophagy by wortmannin significantly inhibited these compounds-mediated cell death. These results indicated that compounds 2a and 2b-induced autophagy led to autophagy-dependent cell death, showing that the compounds can be used as therapeutic agents to treat cancer.

Figure 5D:
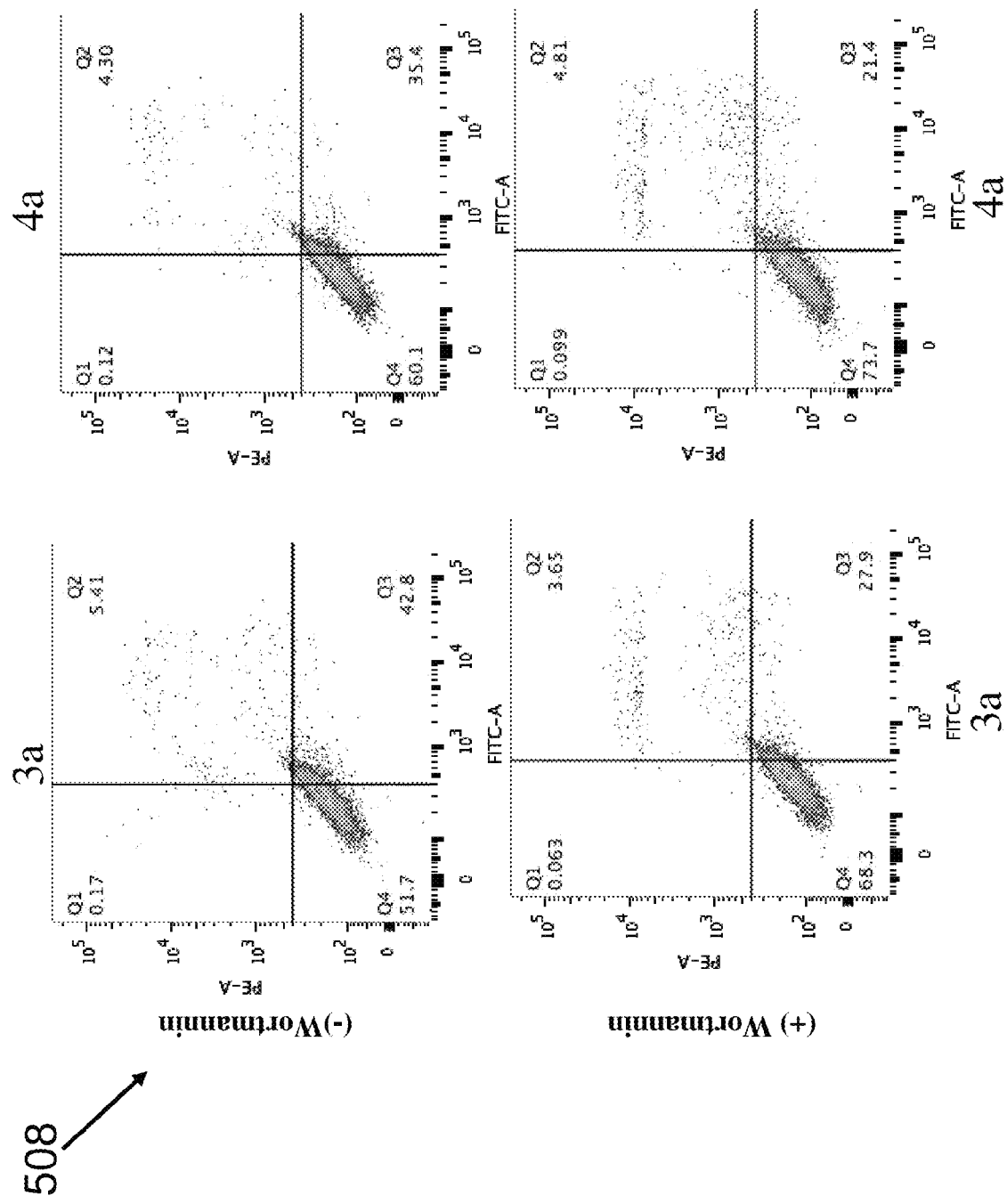
FIG. 5D shows the flow cytometry analysis for HeLa cells treated with compounds 3a and 4a together with Wortmannin or without Wortmannin in accordance with an example embodiment.
Figure 5E:
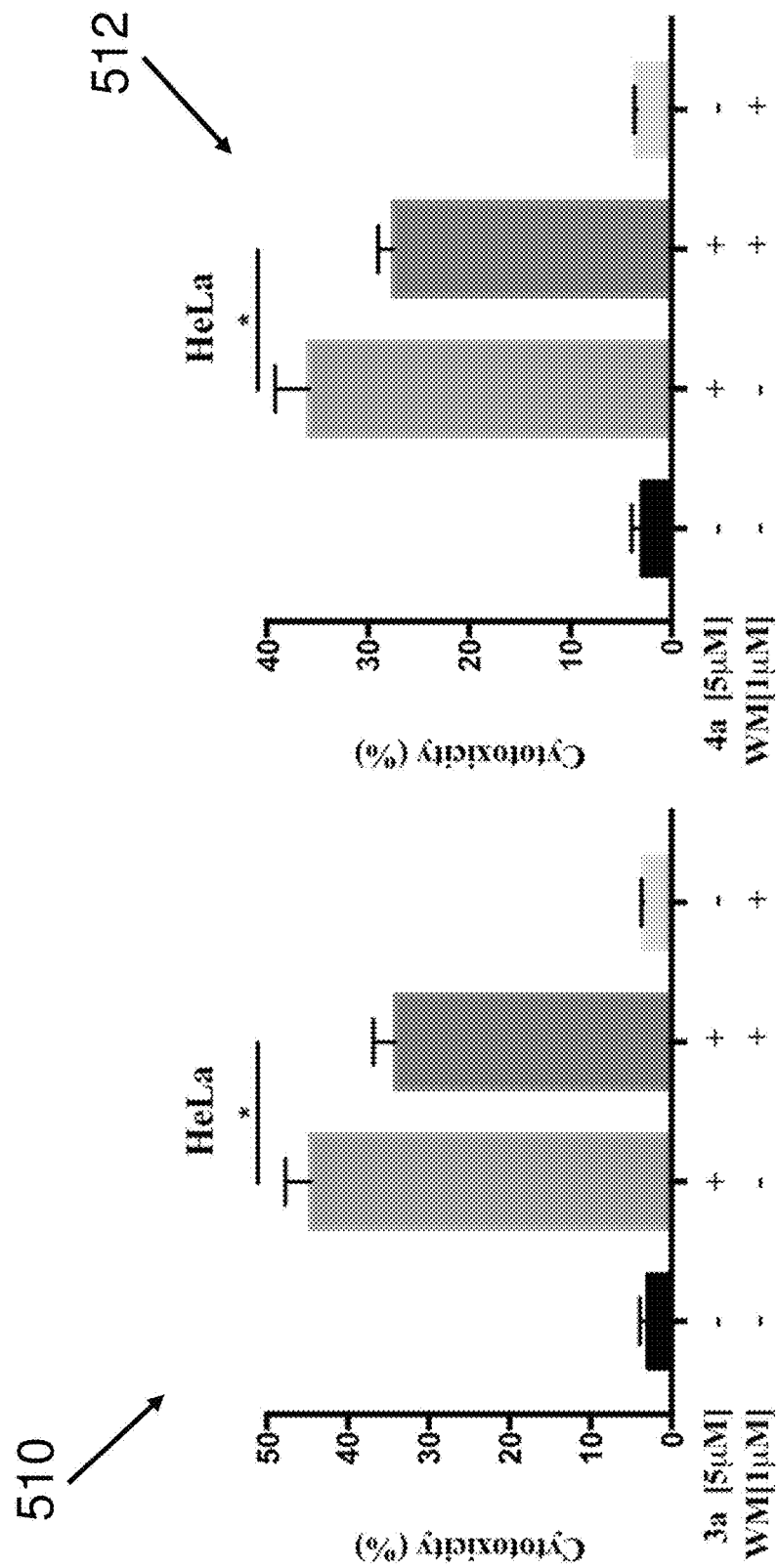
FIG. 5E shows a quantitative graph for the flow cytometry analysis of FIG. 5D illustrating the cytotoxicity of compounds 3a and 4a in HeLa cells in accordance with an example embodiment.

FIG. 5D shows the flow cytometry analysis 508 for HeLa cells treated with compounds 3a and 4a together with Wortmannin or without Wortmannin. FIG. 5E shows graphs 510 and 512 illustrating the quantitative analysis for the flow cytometry analysis.

As shown in FIGS. 5D and 5E, compounds 3a and 4a markedly increased the percentage of cell death, and blocking of autophagy by wortmannin significantly inhibited these compounds-mediated cell death. These results indicated that compounds 3a and 4a-induced autophagy led to autophagy-dependent cell death, showing that the compounds can be used as therapeutic agents to treat cancer.

Dauricine is capable of triggering significant cytotoxicity in vitro towards cancers of liver, cervix, and lung via the induction of autophagic cell death. N-Desmethyldauricine, a derivative of dauricine can increase calcium mobilization, and eventually lead to autophagic cell death in apoptosis-resistant cancer. Compounds 2a-4b were toxic to cancer cells with the cytotoxic effects associated with autophagy activation, similar as dauricine and N-Desmethyldauricine. Compounds 2a, 2b, 3a and 4a demonstrated more potent cytotoxic effect on HeLa cancer cells compared with dauricine and N-Desmethyldauricine. These four compounds showed close $IC_{50}$ values around 6 μM, which were at least 2.3-folds increment of activity compared to that of dauricine (15.53 μM). A calculated log P (c Log P) is routinely used as an assessment of lipophilicity, which reflects the key event of molecular desolvation in transfer from aqueous phases to cell membranes and to protein binding sites. Table 1 showed that c Log P values of these compounds follow the trend of 2a (9.63)>3a (8.58)~4a (8.54)>2b (8.15)>>daurince (6.50).

TABLE 1

| Calculated cLogP values for compounds 2a-4b. | |
|---|---|
| Compounds | cLogP |
| Dau | 6.5 |
| NDau | 6.12 |
| 2a | 9.626 |
| 2b | 8.152 |
| 2c | 6.243 |
| 2d | 6.552 |
| 2e | 7.081 |
| 2f | 7.164 |
| 2g | 6.162 |
| 3a | 8.576 |
| 3b | 7.752 |
| 4a | 8.545 |
| 4b | 6.207 |

Figure 6:
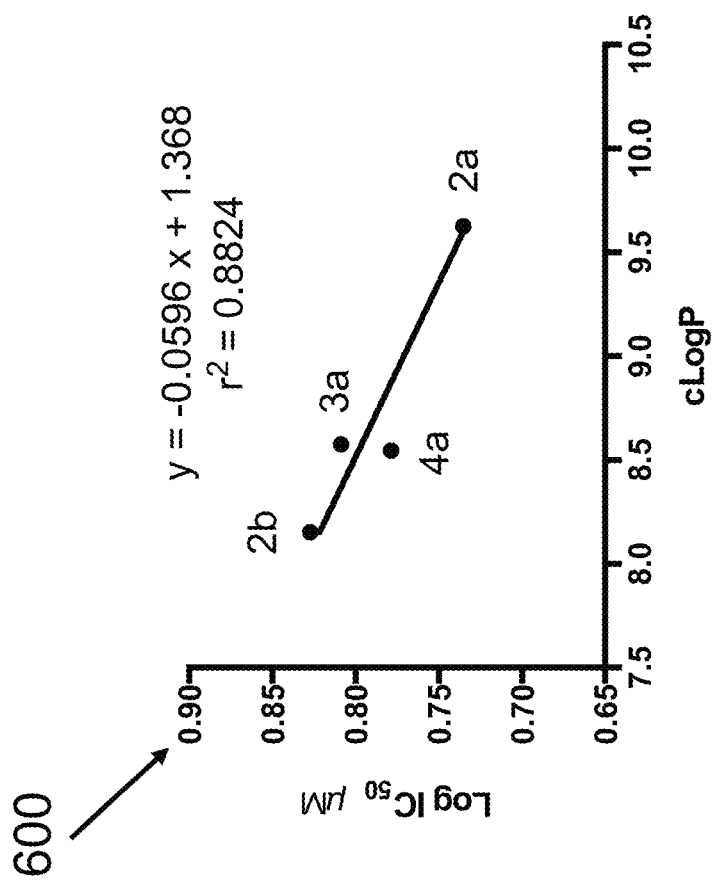
FIG. 6 shows the correlation between Log $IC_{50}$ and cLogP for compounds 2a, 2b, 3a, and 4a in accordance with an example embodiment. Partition coefficients (cLogP) were calculated using ChemDraw Ultra, version 12.0.

These four compounds 2a, 2b, 3a and 4a displayed an inverse linear correlation between log $IC_{50}$ and c Log P values (r2=0.8824), showing that lipophilicity contributes to their cytotoxicity on HeLa cancer cells as shown in the graph 600 of FIG. 6. On the other hand, these four compounds 2a, 2b, 3a, and 4a are having at least one benzene group (phenyl or tolyl) regardless of the nature of the linkage moieties (carbamate, carboxylic ester or sulfonic ester) in their structures. The resonance movement of electrons within these aromatic rings provides extra stability and may explain the more profound cytotoxic effects of these four compounds towards the cancer cells.

Figure 8:
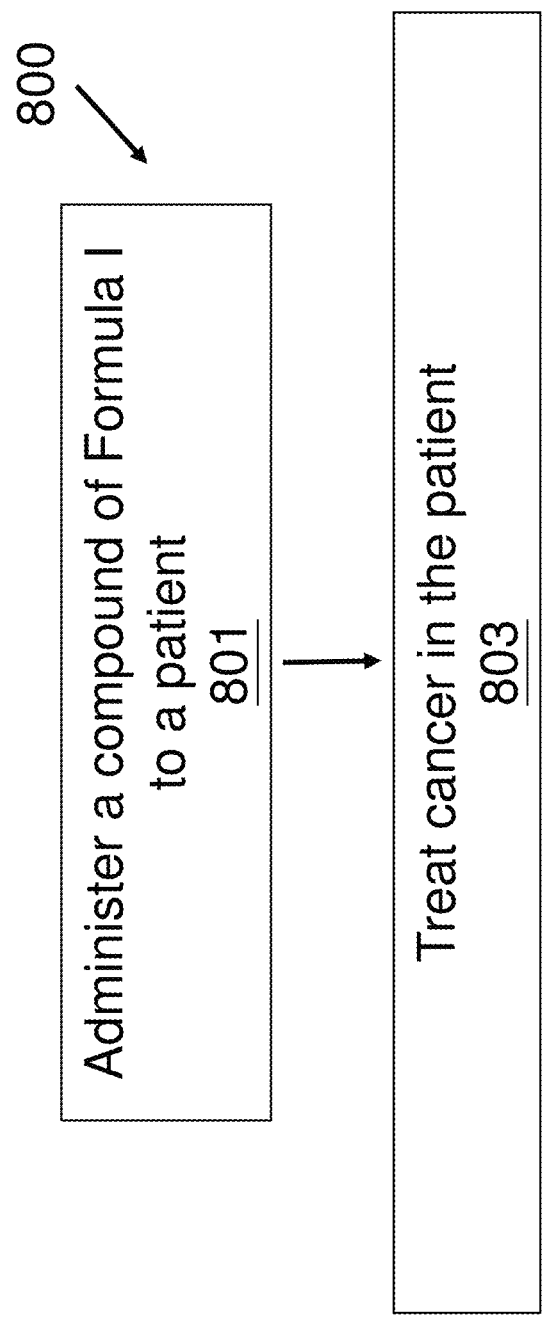
FIG. 8 shows a method of treating cancer in accordance with an example embodiment.

FIG. 8 shows a method 800 of treating cancer in a patient. Block 801 states administering a compound of Formula I to a patient.

In an example embodiment, the compound is administered directly or in pharmaceutical compositions along with suitable carriers or excipients. In one example embodiment, suitable routes of administration may, for example, include oral, rectal, transmucosal, nasal, or intestinal administration and parenteral delivery. The compound or the pharmaceutical composition that includes the compound can be administered locally. For example, the compound can be delivered via injection or in a targeted drug delivery system, such as a depot or sustained release formulation. In one example embodiment, the compound is administered in conjunction with administration of other chemo-drug that treats cancer.

Block 803 states treating cancer in the patient. In an example embodiment, the cancer is apoptosis-resistant cancer. In an example embodiment, the cancer is liver cancer, lung cancer and cervical cancer.

As used herein, the term "administration" or "administering" refers to providing a compound of an example embodiment and/or prodrugs thereof to a person in need of treatment.

As used herein, the term "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fish and the like.

As used herein, the term "pharmaceutically acceptable excipient" refers to pharmacologically inactive substances that are added to a pharmaceutical preparation in addition to the active pharmaceutical ingredient. Pharmaceutically acceptable excipients may take the function of vehicle, diluent, release, disintegration or dissolution modifying agent, absorption enhancer, stabilizer or a manufacturing aid among others.

As used herein, the term "pharmaceutically acceptable salt" refers to pharmaceutically acceptable salts of a compound, which salts are derived from a variety of organic and inorganic counter ions well known in the art, and include, by way of example only, sodium, potassium, calcium, magnesium, ammonium, tetraalkylammonium, and the like; and, when the molecule contains a basic functionality such as —NH$_2$, salts of organic or inorganic acids, such as hydrochloride, hydrobromide, tartrate, mesylate, acetate, trifluoroacetate, maleate, oxalate, and the like.

As used herein, the term "therapeutically effective amount" refers to any amount of a compound which, as compared to a corresponding patient who has not received such amount, results in improved treatment, healing, prevention, or amelioration of a disease, disorder, or side effect, or a decrease in the rate of advancement of a disease or disorder.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "alkyl" refers to saturated monovalent hydrocarbyl groups having from 1 to 10 carbon atoms, more particularly from 1 to 6 carbon atoms, and even more particularly 1 to 3 carbon atoms. This term is exemplified by groups such as methyl, ethyl, n-propyl, iso-propyl, n-butyl, t-butyl, n-pentyl, and the like. The term "$C_1$-$C_6$ alkyl" refers to an alkyl having from 1 to 6 carbon atoms and includes methyl, ethyl, n-propyl, iso-propyl, n-butyl, t-butyl, pentyl, hexyl, and the like.

As used herein, the term "alkoxy" refers to the group "alkyl-O—," which includes, by way of example, $C_1$-$C_6$ alkoxy, such as methoxy, ethoxy, n-propoxy, iso-propoxy, n-butoxy, t-butoxy, sec-butoxy, n-pentoxy, hexoxy, and the like.

As used herein, the term "aryl" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2 benzoxazolinone, 2H-1,4-benzoxazin-3(4H)-one-7-yl, and the like) provided that the point of attachment is the aryl group. Preferred aryls include phenyl and naphthyl.

As used herein, the term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Examples of heteroaryls include but are not limited to, pyridinyl, pyrimidinyl, pyrrolyl, pyrazolyl, indolyl, thiophenyl, thienyl, and furyl.

As used herein, the term "heterocyclyl" refers to a saturated or unsaturated (but not aromatic) group having a single ring or multiple condensed rings, from 1 to 10 carbon atoms, or particularly from 2 to 5 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives. The term "heterocyclyl", by way of example, includes

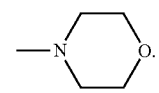

What is claimed is:

1. A compound of Formula I:

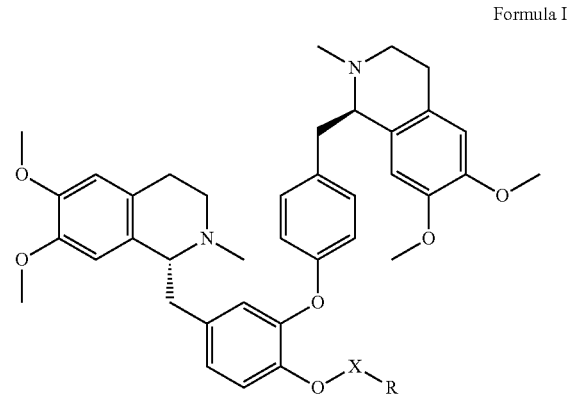

Formula I wherein

R is —NR$_1$R$_2$; X is —CO; and R$_1$ and R$_2$ are both phenyl, or a pharmaceutically acceptable salt of the compound.

2. A pharmaceutical composition comprising a compound of Formula I and a pharmaceutically acceptable excipient,

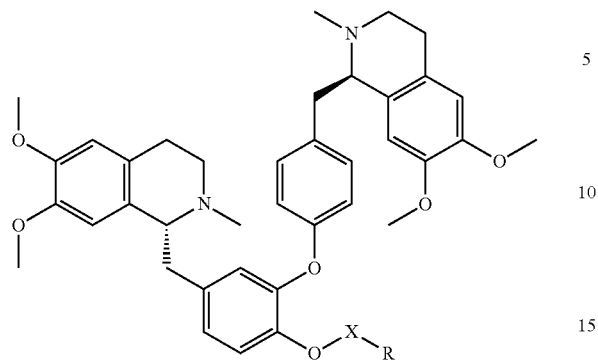
Formula I
wherein
R is —NR₁R₂; X is —CO; and R₁ and R₂ are both phenyl.
* * * * *